US012570981B2

(12) United States Patent
Gaultier et al.

(10) Patent No.: US 12,570,981 B2
(45) Date of Patent: Mar. 10, 2026

(54) GENETICALLY MODIFIED MOUSE WITH CONDITIONAL DELETION OF LRP1 IN OLIGODENDROCYTES

(71) Applicant: University of Virginia Patent Foundation, Charlottesville, VA (US)

(72) Inventors: Alban Gaultier, Charlottesville, VA (US); Anthony Fernandez-Castaneda, Charlottesville, VA (US)

(73) Assignee: University of Virginia Patent Foundation, Charlottesville, VA (US)

( * ) Notice: Subject to any disclaimer, the term of this patent is extended or adjusted under 35 U.S.C. 154(b) by 923 days.

(21) Appl. No.: 16/078,680

(22) PCT Filed: Mar. 21, 2017

(86) PCT No.: PCT/US2017/023340
§ 371 (c)(1),
(2) Date: Aug. 22, 2018

(87) PCT Pub. No.: WO2017/165367
PCT Pub. Date: Sep. 28, 2017

(65) Prior Publication Data

US 2021/0269808 A1 Sep. 2, 2021

Related U.S. Application Data

(60) Provisional application No. 62/311,095, filed on Mar. 21, 2016.

(51) Int. Cl.

| | |
|---|---|
| ***A01K 67/027*** | (2024.01) |
| ***A01K 67/0276*** | (2024.01) |
| ***C07K 14/705*** | (2006.01) |
| ***C12N 5/079*** | (2010.01) |
| ***C12N 15/113*** | (2010.01) |

(52) U.S. Cl.
CPC ...... *C12N 15/1138* (2013.01); *A01K 67/0276* (2013.01); *C07K 14/705* (2013.01); *C12N 5/0622* (2013.01); *A01K 2217/075* (2013.01); *A01K 2217/206* (2013.01); *A01K 2227/105* (2013.01); *A01K 2267/0318* (2013.01)

(58) Field of Classification Search
None
See application file for complete search history.

(56) References Cited

U.S. PATENT DOCUMENTS

| | | | | |
|---|---|---|---|---|
| 4,554,101 | A | 11/1985 | Hopp | |
| 4,946,778 | A | 8/1990 | Ladner et al. | |
| 4,975,369 | A | 12/1990 | Beavers et al. | |
| 5,001,065 | A | 3/1991 | Larrick et al. | |
| 5,075,431 | A | 12/1991 | Shively et al. | |
| 5,081,235 | A | 1/1992 | Shively et al. | |
| 5,169,939 | A | 12/1992 | Gefter et al. | |
| 5,202,238 | A | 4/1993 | Fell et al. | |
| 5,204,244 | A | 4/1993 | Fell et al. | |
| 5,231,026 | A | 7/1993 | Chang | |
| 5,292,867 | A | 3/1994 | Chang | |
| 5,354,847 | A | 10/1994 | Liu et al. | |
| 5,472,693 | A | 12/1995 | Gourlie et al. | |
| 5,482,856 | A | 1/1996 | Fell, Jr. et al. | |
| 5,491,088 | A | 2/1996 | Hellstrom et al. | |
| 5,500,362 | A | 3/1996 | Robinson et al. | |
| 5,502,167 | A | 3/1996 | Waldmann et al. | |
| 5,789,543 | A | 8/1998 | Ingham et al. | |
| 6,207,718 | B1 | 3/2001 | Papadimitriou | |
| 8,704,037 | B2 * | 4/2014 | Selkirk | A61P 25/00 800/13 |
| 2004/0072993 | A1 | 4/2004 | Srivastava | |
| 2014/0142160 | A1 | 5/2014 | Lee et al. | |
| 2014/0161807 | A1 * | 6/2014 | Gonias | A61K 38/18 424/139.1 |
| 2015/0011610 | A1 | 1/2015 | Salzer et al. | |

FOREIGN PATENT DOCUMENTS

WO WO 2007/050866 A2 5/2007

OTHER PUBLICATIONS

Willnow (PNAS, 1995, vol. 92, p. 4537-4541).*
Dutly (1990, "Purified oligodendrocyte precursor cells: interactions with neurons in culture, in Differentiation and Functions of Glial Cells", Proceedings of a Satellite Meeting of the International Society for Neurochemistry held in Rome, Italy, Apr. 19-21, 1989 (G. Levi, ed.; Wiley-Liss), pp. 149-150).*
Gaultier (Journal of Cell Science, 2009, vol. 122, No. 8, p. 1155-1162).*
Herz (Cell, vol. 71, p. 411-421).*
Van der Zee (Genomics, 1994, vol. 23, p. 256-259).*
Hu (Arterioscler Thromb Vasc Biol., 2006, vol. 26, p. 2710-2715).*
Santo (Blood, 2004, vol. 103, p. 3777-3782).*
(Continued)

*Primary Examiner* — Michael C Wilson
(74) *Attorney, Agent, or Firm* — Jenkins, Taylor & Hunt, P.A.

(57) ABSTRACT

Relapsing remitting multiple sclerosis (RRMS) is the most common form of multiple sclerosis, affecting more than 80% of MS patients. RRMS is comprised of two phases: the auto-inflammatory episodes, in which the immune system is actively destroying myelin, alternate with remission phases. Currently there is no cure for this devastating disease. The present disclosure provides compositions and methods useful for inducing remyelination. The methods are useful for promoting remyelination to treat diseases and disorders such as MS. The present disclosure describes compositions and methods useful for inhibiting LRP1 activity. In one aspect, a siRNA against LRP1 can be used. It is disclosed that myelination can be regulated by inhibiting the interaction of LRP1 and p75NTR and that it inhibits activation of Rho-A.

3 Claims, 11 Drawing Sheets

Specification includes a Sequence Listing.

(56) References Cited

OTHER PUBLICATIONS

Boucher (Science, 2003, vol. 300, p. 329-332).*
Li (Circulation, Nov. 25, 2014, vol. 130, No. Suppl. 2, p. 15833).*
Xu (Alzheimer's Res. & Therapy, 2012, vol. 4, No. 12, p. 1-14).*
Lambert (Blood, 2014, 124, 21: 4150).*
Orita (J. Neurosci., 2013, vol. 33, No. 13, p. 5590-5602).*
Pocivavsek (J. Neuroimmunol., 2009, vol. 214, No. 1-2, p. 25-32).*
Lin (eLife, 2017, e30498, p. 1-30).*
Schafer (Cells, 2019, vol. 8, No. 12, p. 1-23).*
Auderset (Frontiers in Cell and Develop. Biol., 2020, vol. 8, Article 564351, p. 1-24).*
Zhao (Neuron, 2010, vol. 65, p. 612-626).*
Dugas (Neuron, 2010, vol. 65, p. 597-611).*
Yang (Develop. Biol., 2013, vol. 378, p. 94-106).*
Zou (J. Neurosci., 2014, vol. 34, p. 15764-15778).*
Hussain (J. Neurosci., 2017, vol. 37, p. 397-412).*
Chun (Cell Death and Disease, 2015, e1748, p. 1-10).*
Mierwa (Neurosci. Letters, 2013, vol. 548, p. 280-285).*
International Search Report and Written Opinion corresponding to International Patent Application No. PCT/US2017/023340 dated Sep. 21, 2017.
International Preliminary Report on Patentability (Chapter I of the Patent Cooperation Treaty) corresponding to International Patent Application No. PCT/US2017/023340 dated Sep. 25, 2018.
Altschul et al. (1990) "Protein database searches for multiple alignments," PNAS, vol. 87, No. 14, pp. 5509-5513.
Altschul et al. (1997) "Gapped BLAST and PSI-BLAST: a new generation of protein database search programs," Nucleic Acids Res., vol. 25, pp. 3389-3402.
Chou et al. (1979) "Prediction of Beta-Turns," Biophys. J., vol. 26, pp. 367-383.
De Kruif et al. (1995) "Selection and Application of Human Single Chain Fv Antibody Fragments from a Semi-synthetic Phage Antibody Display Library with Designed CDR3 Regions," J. Mol. Biol., vol. 248, pp. 97-105.
Devereux et al. (1984) "A comprehensive set of sequence analysis programs for the VAX," Nucleic Acids Res., vol. 12, pp. 387-395.
Huston et al. (1988) "Protein engineering of antibody binding sites: Recovery of specific activity in an anti-digoxin single-chain Fv analogue produced in *Escherichia coli*," PNAS, vol. 85, pp. 5879-5883.
Karlin et al. (1990) "Methods for assessing the statistical significance of molecular sequence features by using general scoring schemes," PNAS, vol. 87, pp. 2264-2268.
Karlin et al. (1993) "Applications and statistics for multiple high-scoring segments in molecular sequences," PNAS, vol. 90, pp. 5873-5877.
Lato et al. (1995) "In vitro selection of RNA lectins: using combinatorial chemistry to interpret ribozyme evolution," Chem. Biol., vol. 2, pp. 291-303.
Tuszynski et al. (1988) "Thrombospondin Promotes Platelet Aggregation," Blood, vol. 72, pp. 109-115.
Wallis et al. (1995) "A Novel RNA Motif for Neomycin Recognition," Chem. Biol. vol. 2, pp. 543-552.
Winter et al. (1991) "Man-Made Antibodies," Nature, vol. 349, p. 293-299.

* cited by examiner

```
                         SEQUENCE LISTING


<160> NUMBER OF SEQ ID NOS: 8

<210> SEQ ID NO 1
<211> LENGTH: 19
<212> TYPE: RNA
<213> ORGANISM: Mus musculus

<400> SEQUENCE: 1

gcuguaacau guucgauga                                                  19


<210> SEQ ID NO 2
<211> LENGTH: 19
<212> TYPE: RNA
<213> ORGANISM: Mus musculus
```

-continued

<400> SEQUENCE: 2
gaccaguguu cucugaaua 19

<210> SEQ ID NO 3
<211> LENGTH: 19
<212> TYPE: RNA
<213> ORGANISM: Mus musculus

<400> SEQUENCE: 3
ggagucacuu acaucaaua 19

<210> SEQ ID NO 4
<211> LENGTH: 19
<212> TYPE: RNA
<213> ORGANISM: Mus musculus

<400> SEQUENCE: 4
gcauuggugu ucagcuuaa 19

<210> SEQ ID NO 5
<211> LENGTH: 19
<212> TYPE: RNA
<213> ORGANISM: Rattus norvegicus

<400> SEQUENCE: 5
uggacaagau cgaacguau 19

<210> SEQ ID NO 6
<211> LENGTH: 19
<212> TYPE: RNA
<213> ORGANISM: Rattus norvegicus

<400> SEQUENCE: 6
ucaauaagca gacgggaga 19

<210> SEQ ID NO 7
<211> LENGTH: 19
<212> TYPE: RNA
<213> ORGANISM: Rattus norvegicus

<400> SEQUENCE: 7
ggacagacgu gacgaccca 19

<210> SEQ ID NO 8
<211> LENGTH: 19
<212> TYPE: RNA
<213> ORGANISM: Rattus norvegicus

<400> SEQUENCE: 8
gggcauuugu gcuggacga 19

GENETICALLY MODIFIED MOUSE WITH CONDITIONAL DELETION OF LRP1 IN OLIGODENDROCYTES

CROSS-REFERENCE TO RELATED APPLICATION

This application is a national stage filing of International Application No. PCT/US2017/023340, filed Mar. 21, 2017, which claims priority under 35 U.S.C. § 119(e) to U.S. Provisional Application Ser. No. 62/311,095 filed Mar. 21, 2016, the disclosures of which are incorporated by reference in their entirety herein.

BACKGROUND

Multiple sclerosis (MS) is a neurodegenerative disease in which myelin of the central nervous system (CNS) is destroyed by a self-reactive immune response, which is accompanied by death of the oligodendrocytes, the myelinating cells of the CNS. Chronic, and/or repeated bouts of, demyelination is a major cause of neuronal dysfunction and neurodegeneration in MS. However, currently approved therapies for MS are aimed at dampening the immune response and do not address the need for stimulation of remyelination. Remyelination is critical for prevention of irreversible changes leading to neuronal death, and is paramount to improving the quality of life of MS patients. The CNS contains a large population of oligodendrocyte precursor cells (OPC) that have the potential to differentiate into mature oligodendrocytes and remyelinate denuded axons. Although OPC are efficiently recruited into MS lesions, OPC differentiation into mature oligodendrocytes and subsequent remyelination is inhibited by myelin debris, which can linger in the area of demyelination. While the mechanism behind suppression of OPC differentiation has remained largely elusive, it has been largely established that this effect is contingent upon the activation of Rho. As such, there has been considerable interest in the use of Rho and Rho-kinase (ROCK) inhibitors in the treatment of MS.

Relapsing remitting MS (RRMS) is the most common form of MS, affecting more than 80% of MS patients. RRMS is comprised of two phases: the auto-inflammatory episodes, in which the immune system is actively destroying myelin, alternate with remission phases. Currently there is no cure for this devastating disease. Approved therapies only slow down disease progression and are directed at taming the destructive autoimmune response during the active phase of the disease. However, there is a complete lack of treatment options designed to promote remyelination during remission and there are no treatments for the progressive form of MS. OPC in the CNS are recruited into the active plaques. However, OPC differentiation into mature oligodendrocytes is blocked by myelin debris in MS lesions. Myelin ligands and the OPC receptors that mediate inhibition of differentiation are currently unknown.

Low density lipoprotein-related protein 1 (LRP1) is a multi-functional cell surface receptor involved in phagocytosis and cell signaling. In neurons, LRP1 contributes to myelin-mediated inhibition of axonal regeneration via activation of Rho, and impairing LRP1 function via genetic silencing or antagonism via receptor associated protein (RAP) blocks activation of Rho and restores neuronal outgrowth.

There is a long felt need in the art for compositions and methods useful for promoting remyelination, or inducing myelination, to treat diseases and disorders such as MS. The present invention satisfies these needs.

SUMMARY

The present disclosure is based in part on the finding that LRP1 is an OPC receptor that contributes to the myelin-mediated blocking of remyelination. LRP1 is an inhibitor of remyelination.

As LRP1 is an established receptor for myelin debris, and this interaction is important for myelin-mediated OPC suppression of differentiation, LRP1 is a therapeutic target in the treatment of MS. It is also disclosed herein that blocking LRP1 restores axon formation on myelin and that MAG is a ligand for LRP1. It is also disclosed herein the remyelination is faster in LRP1-deficient mice.

It is also disclosed herein that deletion of LRP1 in Olig1+ cells enhances remyelination. Additionally, it is disclosed herein that enhancing LRP1 in OPC rescues the myelin-mediated block of OPC differentiation in vitro and that LRP1 has a role in control of myelination and oligodendrocyte development. Therefore, LRP1 and the signaling cascade activated downstream of LRP1 in OPC are new targets for therapy development.

The present disclosure provides compositions and methods useful for inducing remyelination. The methods are useful for promoting remyelination to treat diseases and disorders such as MS. In one embodiment, the present disclosure comprises compositions and methods useful for inhibiting LRP1 activity, function, expression, levels, or synthesis. The compositions and methods disclosed herein can be used to inhibit LRP1 in oligodendrocyte precursor cells.

In one aspect, LRP1 is inhibited directly. In one aspect, its activity is inhibited upstream in its signaling pathway. In one aspect, its activity is inhibited downstream in its signaling pathway. The silencing of LRP1 can lead to inhibition of the pathological activation of Rho-A.

In one aspect, a siRNA against LRP1 (also referred to herein as a LRP1-targeting siRNA or siLRP1) can be used. The siRNA can target one or more sequences selected from the group consisting of SEQ ID NOs: 1-8. For example, the siRNA can target one or more sequences selected from the group consisting of SEQ ID NOs: 1-4 or one or more sequences selected from the group consisting of SEQ ID NOs: 5-8. In one embodiment, the present disclosure provides compositions and methods useful for inhibiting the activation of Rho-A.

The sequences of the invention are:

```
                          SEQ ID NO: 1
gcuguaacauguucgauga

                          SEQ ID NO: 2
gaccaguguucucugaaua

                          SEQ ID NO: 3
ggagucacuuacaucaaua

                          SEQ ID NO: 4
gcauugguguucagcuuaa

                          SEQ ID NO: 5
uggacaagaucgaacguau

                          SEQ ID NO: 6
ucaauaagcagacgggaga
```

-continued

SEQ ID NO: 7 ggacagacgugacgaccca

SEQ ID NO: 8 gggcauuugugcuggacga

In one embodiment, the compositions and methods are useful for treating myelin-mediated inhibition of axonal regeneration. In one aspect, treatment is useful in the presence of myelin debris. In one embodiment, the compositions and methods of the disclosure are useful for maintaining neuronal viability. In another embodiment, the compositions and methods are useful for increasing neuronal viability.

One of ordinary skill in the art will appreciate that the agents and compounds can be administered in a variety of ways based on, for example, the location of the disease, disorder, or injury, and the cell types targeted for treatment.

DETAILED DESCRIPTION

Abbreviations and Acronyms

Figure 1A:
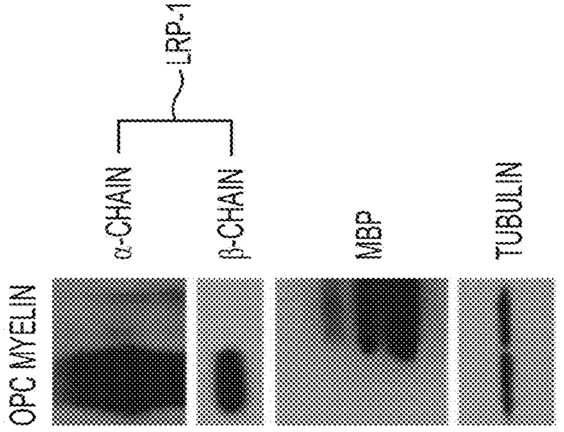
FIG. 1A is an immunoblot for LRP1 expression in OPC and purified myelin.

EAE—experimental autoimmune encephalomyelitis
LRP1—LDL Receptor—related Protein—1
NTC—non—targeting control
RAP—receptor associated protein
siLRP1—siRNA against LRP1
siRNA—small interfering RNA

Definitions

The following terminology will be used in accordance with the definitions set forth below.

The articles "a" and "an" are used herein to refer to one or to more than one (i.e., to at least one) of the grammatical object of the article. By way of example, "an element" means one element or more than one element.

The term "about," as used herein, means approximately, in the region of, roughly, or around. When the term "about" is used in conjunction with a numerical range, it modifies that range by extending the boundaries above and below the numerical values set forth. In general, the term "about" is used herein to modify a numerical value above and below the stated value by a variance of 10%. In one aspect, the term "about" means plus or minus 20% of the numerical value of the number with which it is being used. Therefore, about 50% means in the range of 45%-55%. Numerical ranges recited herein by endpoints include all numbers and fractions subsumed within that range (e.g. 1 to 5 includes 1, 1.5, 2, 2.75, 3, 3.90, 4, and 5). It is also to be understood that all numbers and fractions thereof are presumed to be modified by the term "about."

The terms "additional therapeutically active compound" or "additional therapeutic agent", as used in the context of the present disclosure, refers to the use or administration of a compound for an additional therapeutic use for a particular injury, disease, or disorder being treated. Such a compound, for example, could include one being used to treat an unrelated disease or disorder, or a disease or disorder which may not be responsive to the primary treatment for the injury, disease or disorder being treated.

As used herein, the term "adjuvant" refers to a substance that elicits an enhanced immune response when used in combination with a specific antigen.

As use herein, the terms "administration of" and or "administering" a compound should be understood to mean providing a compound of the disclosure or a prodrug of a compound of the disclosure to a subject in need of treatment.

As used herein, the term "aerosol" refers to suspension in the air. In particular, aerosol refers to the particlization or atomization of a formulation of the disclosure and its suspension in the air.

As used herein, an "agonist" is a composition of matter which, when administered to a mammal such as a human, enhances or extends a biological activity attributable to the level or presence of a target compound or molecule of interest in the mammal.

The term "alterations in peptide structure" as used herein refers to changes including, but not limited to, changes in sequence, and post-translational modification.

An "antagonist" is a composition of matter which when administered to a mammal such as a human, inhibits a biological activity attributable to the level or presence of a compound or molecule of interest in the mammal.

As used herein, "alleviating a disease or disorder symptom," means reducing the severity of the symptom or the frequency with which such a symptom is experienced by a patient, or both.

As used herein, amino acids are represented by the full name thereof, by the three letter code corresponding thereto, or by the one-letter code corresponding thereto, as indicated in the following table:

| Full Name | Three-Letter Code | One-Letter Code |
|---|---|---|
| Aspartic Acid | Asp | D |
| Glutamic Acid | Glu | E |
| Lysine | Lys | K |
| Arginine | Arg | R |
| Histidine | His | H |
| Tyrosine | Tyr | Y |
| Cysteine | Cys | C |
| Asparagine | Asn | N |
| Glutamine | Gln | Q |
| Serine | Ser | S |
| Threonine | Thr | T |
| Glycine | Gly | G |
| Alanine | Ala | A |
| Valine | Val | V |
| Leucine | Leu | L |
| Isoleucine | Ile | I |
| Methionine | Met | M |
| Proline | Pro | P |
| Phenylalanine | Phe | F |
| Tryptophan | Trp | W |

The term "amino acid" is used interchangeably with "amino acid residue," and may refer to a free amino acid and to an amino acid residue of a peptide. It will be apparent from the context in which the term is used whether it refers to a free amino acid or a residue of a peptide.

Amino acids have the following general structure:

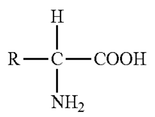

Amino acids may be classified into seven groups on the basis of the side chain R: (1) aliphatic side chains, (2) side chains containing a hydroxylic (OH) group, (3) side chains containing sulfur atoms, (4) side chains containing an acidic or amide group, (5) side chains containing a basic group, (6) side chains containing an aromatic ring, and (7) proline, an amino acid in which the side chain is fused to the amino group.

The nomenclature used to describe the peptide compounds of the present disclosure follows the conventional practice wherein the amino group is presented to the left and the carboxy group to the right of each amino acid residue. In the formulae representing selected specific embodiments of the present disclosure, the amino- and carboxy-terminal groups, although not specifically shown, will be understood to be in the form they would assume at physiologic pH values, unless otherwise specified.

The term "basic" or "positively charged" amino acid, as used herein, refers to amino acids in which the R groups have a net positive charge at pH 7.0, and include, but are not limited to, the standard amino acids lysine, arginine, and histidine.

As used herein, an "analog" of a chemical compound is a compound that, by way of example, resembles another in structure but is not necessarily an isomer (e.g., 5-fluorouracil is an analog of thymine).

The term "antibody," as used herein, refers to an immunoglobulin molecule which is able to specifically bind to a specific epitope on an antigen. Antibodies can be intact immunoglobulins derived from natural sources or from recombinant sources and can be immunoreactive portions of intact immunoglobulins. Antibodies are typically tetramers of immunoglobulin molecules. The antibodies in the present disclosure may exist in a variety of forms including, for example, polyclonal antibodies, monoclonal antibodies, Fv, Fab and $F(ab)_2$, as well as single chain antibodies and humanized antibodies.

The term "antibody" refers to polyclonal and monoclonal antibodies and derivatives thereof (including chimeric, synthesized, humanized and human antibodies), including an entire immunoglobulin or antibody or any functional fragment of an immunoglobulin molecule which binds to the target antigen and or combinations thereof. Examples of such functional entities include complete antibody molecules, antibody fragments, such as $F_v$, single chain $F_v$, complementarity determining regions (CDRs), $V_L$ (light chain variable region), $V_H$ (heavy chain variable region), Fab, $F(ab')_2$ and any combination of those or any other functional portion of an immunoglobulin peptide capable of binding to target antigen.

Antibodies exist, e.g., as intact immunoglobulins or as a number of well characterized fragments produced by digestion with various peptidases. Thus, for example, pepsin digests an antibody below the disulfide linkages in the hinge region to produce $F(ab')_2$ a dimer of Fab which itself is a light chain joined to $V_H$-$C_{H1}$ by a disulfide bond. The $F(ab')_2$ may be reduced under mild conditions to break the disulfide linkage in the hinge region, thereby converting the $F(ab')_2$ dimer into an $Fab_1$ monomer. The $Fab_1$ monomer is essentially an Fab with part of the hinge region (see, FUNDAMENTAL IMMUNOLOGY, 3RD ED., W. E. Paul, ed, Raven Press, N.Y. (1993)). While various antibody fragments are defined in terms of the digestion of an intact antibody, one of skill will appreciate that such fragments may be synthesized de novo either chemically or by utilizing recombinant DNA methodology. Thus, the term antibody, as used herein, also includes antibody fragments either produced by the modification of whole antibodies or those synthesized de novo using recombinant DNA methodologies.

An "antibody heavy chain," as used herein, refers to the larger of the two types of polypeptide chains present in all antibody molecules.

An "antibody light chain," as used herein, refers to the smaller of the two types of polypeptide chains present in all antibody molecules.

The term "single chain antibody" refers to an antibody wherein the genetic information encoding the functional fragments of the antibody is located in a single contiguous length of DNA. For a thorough description of single chain antibodies, see Bire, et al., Science 242:423 (1988) and Huston, et al., Proc. Nat'l Acad. Sci. USA 85:5879 (1988).

The term "humanized" refers to an antibody wherein the constant regions have at least about 80% or greater homology to human immunoglobulin. Additionally, some of the nonhuman, such as murine, variable region amino acid residues can be modified to contain amino acid residues of human origin.

Humanized antibodies have been referred to as "reshaped" antibodies. Manipulation of the complementarity-determining regions (CDR) is a way of achieving humanized antibodies. See, for example, Jones, et al., Nature 321:522 (1988) and Riechmann, et al., Nature 332:323 (1988), both of which are incorporated by reference herein. For a review article concerning humanized antibodies, see Winter & Milstein, Nature 349:293 (1991), incorporated by reference herein.

By the term "synthetic antibody" as used herein, is meant an antibody which is generated using recombinant DNA technology, such as, for example, an antibody expressed by a bacteriophage as described herein. The term should also be construed to mean an antibody which has been generated by the synthesis of a DNA molecule encoding the antibody and which DNA molecule expresses an antibody protein, or an amino acid sequence specifying the antibody, wherein the DNA or amino acid sequence has been obtained using synthetic DNA or amino acid sequence technology which is available and well known in the art.

The term "antigen" as used herein is defined as a molecule that provokes an immune response. This immune response may involve either antibody production, or the activation of specific immunologically-competent cells, or both. An antigen can be derived from organisms, subunits of proteins/antigens, killed or inactivated whole cells or lysates.

The term "antimicrobial agents" as used herein refers to any naturally-occurring, synthetic, or semi-synthetic compound or composition or mixture thereof, which is safe for human or animal use as practiced in the methods of this disclosure, and is effective in killing or substantially inhibiting the growth of microbes. "Antimicrobial" as used herein, includes antibacterial, antifungal, and antiviral agents.

As used herein, the term "antisense oligonucleotide" or antisense nucleic acid means a nucleic acid polymer, at least a portion of which is complementary to a nucleic acid which is present in a normal cell or in an affected cell. "Antisense" refers particularly to the nucleic acid sequence of the non-coding strand of a double stranded DNA molecule encoding a protein, or to a sequence which is substantially homologous to the non-coding strand. As defined herein, an antisense sequence is complementary to the sequence of a double stranded DNA molecule encoding a protein. It is not necessary that the antisense sequence be complementary solely to the coding portion of the coding strand of the DNA molecule. The antisense sequence may be complementary to regulatory sequences specified on the coding strand of a DNA molecule encoding a protein, which regulatory sequences control expression of the coding sequences. The antisense oligonucleotides of the disclosure include, but are not limited to, phosphorothioate oligonucleotides and other modifications of oligonucleotides.

An "aptamer" is a compound that is selected in vitro to bind preferentially to another compound (for example, the identified proteins herein). Often, aptamers are nucleic acids or peptides because random sequences can be readily generated from nucleotides or amino acids (both naturally occurring and synthetically made) in large numbers but of course they need not be limited to these.

The term "binding" refers to the adherence of molecules to one another, such as, but not limited to, enzymes to substrates, ligands to receptors, antibodies to antigens, DNA binding domains of proteins to DNA, and DNA or RNA strands to complementary strands.

"Binding partner," as used herein, refers to a molecule capable of binding to another molecule.

The term "biocompatible", as used herein, refers to a material that does not elicit a substantial detrimental response in the host.

As used herein, the term "biologically active fragments" or "bioactive fragment" of the polypeptides encompasses natural or synthetic portions of the full-length protein that are capable of specific binding to their natural ligand or of performing the function of the protein.

The term "biological sample," as used herein, refers to samples obtained from a subject, including, but not limited to, sputum, mucus, phlegm, tissues, biopsies, cerebrospinal fluid, blood, serum, plasma, other blood components, gastric aspirates, throat swabs, pleural effusion, peritoneal fluid, follicular fluid, ascites, skin, hair, tissue, blood, plasma, cells, saliva, sweat, tears, semen, stools, Pap smears, and urine. One of skill in the art will understand the type of sample needed.

A "biomarker" or "marker" is a specific biochemical in the body which has a particular molecular feature that makes it useful for measuring the progress of disease or the effects of treatment, or for measuring a process of interest.

The term "cancer", as used herein, is defined as proliferation of cells whose unique trait (loss of normal controls) results in unregulated growth, lack of differentiation, local tissue invasion, and metastasis. Examples include but are not limited to, melanoma, breast cancer, prostate cancer, ovarian cancer, uterine cancer, cervical cancer, skin cancer, pancreatic cancer, colorectal cancer, renal cancer and lung cancer.

As used herein, the term "carrier molecule" refers to any molecule that is chemically conjugated to a molecule of interest.

The term "cell surface protein" means a protein found where at least part of the protein is exposed at the outer aspect of the cell membrane. Examples include growth factor receptors.

As used herein, the term "chemically conjugated," or "conjugating chemically" refers to linking the antigen to the carrier molecule. This linking can occur on the genetic level using recombinant technology, wherein a hybrid protein may be produced containing the amino acid sequences, or portions thereof, of both the antigen and the carrier molecule. This hybrid protein is produced by an oligonucleotide sequence encoding both the antigen and the carrier molecule, or portions thereof. This linking also includes covalent bonds created between the antigen and the carrier protein using other chemical reactions, such as, but not limited to glutaraldehyde reactions. Covalent bonds may also be created using a third molecule bridging the antigen to the carrier molecule. These cross-linkers are able to react with groups, such as but not limited to, primary amines, sulfhydryls, carbonyls, carbohydrates, or carboxylic acids, on the antigen and the carrier molecule. Chemical conjugation also includes non-covalent linkage between the antigen and the carrier molecule.

A "coding region" of a gene consists of the nucleotide residues of the coding strand of the gene and the nucleotides of the non-coding strand of the gene which are homologous with or complementary to, respectively, the coding region of an mRNA molecule which is produced by transcription of the gene.

The term "competitive sequence" refers to a peptide or a modification, fragment, derivative, or homolog thereof that competes with another peptide for its cognate binding site.

"Complementary" as used herein refers to the broad concept of subunit sequence complementarity between two nucleic acids, e.g., two DNA molecules. When a nucleotide position in both of the molecules is occupied by nucleotides normally capable of base pairing with each other, then the nucleic acids are considered to be complementary to each other at this position. Thus, two nucleic acids are complementary to each other when a substantial number (at least 50%) of corresponding positions in each of the molecules are occupied by nucleotides which normally base pair with each other (e.g., A:T and G:C nucleotide pairs). Thus, it is known that an adenine residue of a first nucleic acid region is capable of forming specific hydrogen bonds ("base pairing") with a residue of a second nucleic acid region which is antiparallel to the first region if the residue is thymine or uracil. Similarly, it is known that a cytosine residue of a first nucleic acid strand is capable of base pairing with a residue of a second nucleic acid strand which is antiparallel to the first strand if the residue is guanine. A first region of a nucleic acid is complementary to a second region of the same or a different nucleic acid if, when the two regions are arranged in an antiparallel fashion, at least one nucleotide residue of the first region is capable of base pairing with a residue of the second region. Preferably, the first region comprises a first portion and the second region comprises a second portion, whereby, when the first and second portions are arranged in an antiparallel fashion, at least about 50%, and preferably at least about 75%, at least about 90%, or at least about 95% of the nucleotide residues of the first portion are capable of base pairing with nucleotide residues in the second portion. More preferably, all nucleotide residues of the first portion are capable of base pairing with nucleotide residues in the second portion.

A "compound," as used herein, refers to any type of substance or agent that is commonly considered a drug, or a candidate for use as a drug, as well as combinations and mixtures of the above.

A "computer-readable medium" is an information storage medium that can be accessed by a computer using a commercially available or custom-made interface. Exemplary computer-readable media include memory (e.g., RAM, ROM, flash memory, etc.), optical storage media (e.g., CD-ROM), magnetic storage media (e.g., computer hard drives, floppy disks, etc.), punch cards, or other commercially available media. Information may be transferred between a system of interest and a medium, between computers, or between computers and the computer-readable medium for storage or access of stored information. Such transmission can be electrical, or by other available methods, such as IR links, wireless connections, etc.

As used herein, the term "conservative amino acid substitution" is defined herein as an amino acid exchange within one of the following five groups:

I. Small aliphatic, nonpolar or slightly polar residues:
  Ala, Ser, Thr, Pro, Gly;
II. Polar, negatively charged residues and their amides:
  Asp, Asn, Glu, Gln;
III. Polar, positively charged residues:
  His, Arg, Lys;
IV. Large, aliphatic, nonpolar residues:
  Met, Leu, Ile, Val, Cys
V. Large, aromatic residues:
  Phe, Tyr, Trp A "control" cell is a cell having the same cell type as a test cell. The control cell may, for example, be examined at precisely or nearly the same time the test cell is examined. The control cell may also, for example, be examined at a time distant from the time at which the test cell is examined, and the results of the examination of the control cell may be recorded so that the recorded results may be compared with results obtained by examination of a test cell.

A "test" cell is a cell being examined.

As used herein, a "derivative" of a compound refers to a chemical compound that may be produced from another compound of similar structure in one or more steps, as in replacement of H by an alkyl, acyl, or amino group.

As used herein "detachment-induced chemoresistance" refers to the change in cancer cells that occurs when they become resistant to chemotherapy following a change in their interactions with the extracellular matrix.

The use of the word "detect" and its grammatical variants refers to measurement of the species without quantification, whereas use of the word "determine" or "measure" with their grammatical variants are meant to refer to measurement of the species with quantification. The terms "detect" and "identify" are used interchangeably herein.

As used herein, a "detectable marker" or a "reporter molecule" is an atom or a molecule that permits the specific detection of a compound comprising the marker in the presence of similar compounds without a marker. Detectable markers or reporter molecules include, e.g., radioactive isotopes, antigenic determinants, enzymes, nucleic acids available for hybridization, chromophores, fluorophores, chemiluminescent molecules, electrochemically detectable molecules, and molecules that provide for altered fluorescence-polarization or altered light-scattering.

A "disease" is a state of health of an animal wherein the animal cannot maintain homeostasis, and wherein if the disease is not ameliorated then the animal's health continues to deteriorate.

In contrast, a "disorder" in an animal is a state of health in which the animal is able to maintain homeostasis, but in which the animal's state of health is less favorable than it would be in the absence of the disorder. Left untreated, a disorder does not necessarily cause a further decrease in the animal's state of health.

As used herein, the term "domain" refers to a part of a molecule or structure that shares common physicochemical features, such as, but not limited to, hydrophobic, polar, globular and helical domains or properties such as ligand binding, signal transduction, cell penetration and the like. Specific examples of binding domains include, but are not limited to, DNA binding domains and ATP binding domains.

As used herein, an "effective amount" or "therapeutically effective amount" means an amount sufficient to produce a selected effect, such as alleviating symptoms of a disease or disorder. In the context of administering compounds in the form of a combination, such as multiple compounds, the amount of each compound, when administered in combination with another compound(s), may be different from when that compound is administered alone. Thus, an effective amount of a combination of compounds refers collectively to the combination as a whole, although the actual amounts of each compound may vary. The term "more effective" means that the selected effect is alleviated to a greater extent by one treatment relative to the second treatment to which it is being compared.

As used herein, the term "effector domain" refers to a domain capable of directly interacting with an effector molecule, chemical, or structure in the cytoplasm which is capable of regulating a biochemical pathway.

The term "elixir," as used herein, refers in general to a clear, sweetened, alcohol-containing, usually hydroalcoholic liquid containing flavoring substances and sometimes active medicinal agents.

"Encoding" refers to the inherent property of specific sequences of nucleotides in a polynucleotide, such as a gene, a cDNA, or an mRNA, to serve as templates for synthesis of other polymers and macromolecules in biological processes having either a defined sequence of nucleotides (i.e., IRNA, tRNA and mRNA) or a defined sequence of amino acids and the biological properties resulting therefrom. Thus, a gene encodes a protein if transcription and translation of mRNA corresponding to that gene produces the protein in a cell or other biological system. Both the coding strand, the nucleotide sequence of which is identical to the mRNA sequence and is usually provided in sequence listings, and the non-coding strand, used as the template for transcription of a gene or cDNA, can be referred to as encoding the protein or other product of that gene or cDNA.

An "enhancer" is a DNA regulatory element that can increase the efficiency of transcription, regardless of the distance or orientation of the enhancer relative to the start site of transcription.

The term "epitope" as used herein is defined as small chemical groups on the antigen molecule that can elicit and react with an antibody. An antigen can have one or more epitopes. Most antigens have many epitopes; i.e., they are multivalent. In general, an epitope is roughly five amino acids or sugars in size. One skilled in the art understands that generally the overall three-dimensional structure, rather than the specific linear sequence of the molecule, is the main criterion of antigenic specificity.

As used herein, an "essentially pure" preparation of a particular protein or peptide is a preparation wherein at least about 95%, and preferably at least about 99%, by weight, of the protein or peptide in the preparation is the particular protein or peptide.

Use of the term "fibronectin peptide" refers to fibronectin or a fragment thereof.

A "fragment" or "segment" is a portion of an amino acid sequence, comprising at least one amino acid, or a portion of a nucleic acid sequence comprising at least one nucleotide. The terms "fragment" and "segment" are used interchangeably herein.

As used herein, the term "fragment," as applied to a protein or peptide, can ordinarily be at least about 3-15 amino acids in length, at least about 15-25 amino acids, at least about 25-50 amino acids in length, at least about 50-75 amino acids in length, at least about 75-100 amino acids in length, and greater than 100 amino acids in length.

As used herein, the term "fragment" as applied to a nucleic acid, may ordinarily be at least about 20 nucleotides in length, typically, at least about 50 nucleotides, more typically, from about 50 to about 100 nucleotides, preferably, at least about 100 to about 200 nucleotides, even more preferably, at least about 200 nucleotides to about 300 nucleotides, yet even more preferably, at least about 300 to about 350, even more preferably, at least about 350 nucleotides to about 500 nucleotides, yet even more preferably, at least about 500 to about 600, even more preferably, at least about 600 nucleotides to about 620 nucleotides, yet even more preferably, at least about 620 to about 650, and most preferably, the nucleic acid fragment will be greater than about 650 nucleotides in length.

As used herein, a "functional" biological molecule is a biological molecule in a form in which it exhibits a property by which it is characterized. A functional enzyme, for example, is one which exhibits the characteristic catalytic activity by which the enzyme is characterized.

"Homologous" as used herein, refers to the subunit sequence similarity between two polymeric molecules, e.g., between two nucleic acid molecules, e.g., two DNA molecules or two RNA molecules, or between two polypeptide molecules. When a subunit position in both of the two molecules is occupied by the same monomeric subunit, e.g., if a position in each of two DNA molecules is occupied by adenine, then they are homologous at that position. The homology between two sequences is a direct function of the number of matching or homologous positions, e.g., if half (e.g., five positions in a polymer ten subunits in length) of the positions in two compound sequences are homologous then the two sequences are 50% homologous, if 90% of the positions, e.g., 9 of 10, are matched or homologous, the two sequences share 90% homology. By way of example, the DNA sequences 3'ATTGCC5' and 3'TATGGC share 50% homology.

As used herein, "homology" is used synonymously with "identity."

The determination of percent identity between two nucleotide or amino acid sequences can be accomplished using a mathematical algorithm. For example, a mathematical algorithm useful for comparing two sequences is the algorithm of Karlin and Altschul (1990, Proc. Natl. Acad. Sci. USA 87:2264-2268), modified as in Karlin and Altschul (1993, Proc. Natl. Acad. Sci. USA 90:5873-5877). This algorithm is incorporated into the NBLAST and XBLAST programs of Altschul, et al. (1990, J. Mol. Biol. 215:403-410), and can be accessed, for example at the National Center for Biotechnology Information (NCBI) world wide web site having the universal resource locator using the BLAST tool at the NCBI website. BLAST nucleotide searches can be performed with the NBLAST program (designated "blastn" at the NCBI web site), using the following parameters: gap penalty=5; gap extension penalty=2; mismatch penalty=3; match reward=1; expectation value 10.0; and word size=11 to obtain nucleotide sequences homologous to a nucleic acid described herein. BLAST protein searches can be performed with the XBLAST program (designated "blastn" at the NCBI web site) or the NCBI "blastp" program, using the following parameters: expectation value 10.0, BLOSUM62 scoring matrix to obtain amino acid sequences homologous to a protein molecule described herein. To obtain gapped alignments for comparison purposes, Gapped BLAST can be utilized as described in Altschul et al. (1997, Nucleic Acids Res. 25:3389-3402). Alternatively, PSI-Blast or PHI-Blast can be used to perform an iterated search which detects distant relationships between molecules (Id.) and relationships between molecules which share a common pattern. When utilizing BLAST, Gapped BLAST, PSI-Blast, and PHI-Blast programs, the default parameters of the respective programs (e.g., XBLAST and NBLAST) can be used.

The percent identity between two sequences can be determined using techniques similar to those described above, with or without allowing gaps. In calculating percent identity, typically exact matches are counted.

As used herein, the term "hybridization" is used in reference to the pairing of complementary nucleic acids. Hybridization and the strength of hybridization (i.e., the strength of the association between the nucleic acids) is impacted by such factors as the degree of complementarity between the nucleic acids, stringency of the conditions involved, the length of the formed hybrid, and the G:C ratio within the nucleic acids.

As used herein, the term "inhaler" refers both to devices for nasal and pulmonary administration of a drug, e.g., in solution, powder and the like. For example, the term "inhaler" is intended to encompass a propellant driven inhaler, such as is used to administer antihistamine for acute asthma attacks, and plastic spray bottles, such as are used to administer decongestants.

The term "inhibit," as used herein, refers to the ability of a compound, agent, or method to reduce or impede a described function, level, activity, rate, etc., based on the context in which the term "inhibit" is used. Preferably, inhibition is by at least 10%, more preferably by at least 25%, even more preferably by at least 50%, and most preferably, the function is inhibited by at least 75%. The term "inhibit" is used interchangeably with "reduce" and "block."

The term "inhibit a complex," as used herein, refers to inhibiting the formation of a complex or interaction of two or more proteins, as well as inhibiting the function or activity of the complex. The term also encompasses disrupting a formed complex. However, the term does not imply that each and every one of these functions must be inhibited at the same time.

The term "inhibit a protein," as used herein, refers to any method or technique which inhibits protein synthesis, levels, activity, or function, as well as methods of inhibiting the induction or stimulation of synthesis, levels, activity, or function of the protein of interest. The term also refers to any metabolic or regulatory pathway which can regulate the synthesis, levels, activity, or function of the protein of interest. The term includes binding with other molecules and complex formation. Therefore, the term "protein inhibitor" refers to any agent or compound, the application of which results in the inhibition of protein function or protein pathway function. However, the term does not imply that each and every one of these functions must be inhibited at the same time.

As used herein "injecting or applying" includes administration of a compound of the disclosure by any number of routes and means including, but not limited to, topical, oral, buccal, intravenous, intramuscular, intra-arterial, intramedullary, intrathecal, intraventricular, transdermal, subcutaneous, intraperitoneal, intranasal, enteral, topical, sublingual, vaginal, ophthalmic, pulmonary, or rectal means. Compounds or agents of the disclosure can be administered to a subject by these means when appropriate.

As used herein, an "instructional material" includes a publication, a recording, a diagram, or any other medium of expression which can be used to communicate the usefulness of the peptide of the disclosure in the kit for effecting alleviation of the various diseases or disorders recited herein. Optionally, or alternately, the instructional material may describe one or more methods of alleviating the diseases or disorders in a cell or a tissue of a mammal. The instructional material of the kit of the disclosure may, for example, be affixed to a container which contains the identified compound or be shipped together with a container which contains the identified compound. Alternatively, the instructional material may be shipped separately from the container with the intention that the instructional material and the compound be used cooperatively by the recipient.

As used herein, the term "invasive," or "metastasis" as used herein, refers to any migration of cells, especially to invasive cancer cells or tumor cells. The term applies to normally invasive cells such as wound-healing fibroblasts and also to cells that migrate abnormally. Although the term is not to be limited by any mechanistic rationale, such cells are thought to migrate by defeating the body's means for keeping them sufficiently "in place" to function normally. Such cells are "invasive" if they migrate abnormally within a tissue or tumor, or escape the tissue, or invade other tissues.

An "isolated nucleic acid" refers to a nucleic acid segment or fragment which has been separated from sequences which flank it in a naturally occurring state, e.g., a DNA fragment which has been removed from the sequences which are normally adjacent to the fragment, e.g., the sequences adjacent to the fragment in a genome in which it naturally occurs. The term also applies to nucleic acids which have been substantially purified from other components which naturally accompany the nucleic acid, e.g., RNA or DNA or proteins, which naturally accompany it in the cell. The term therefore includes, for example, a recombinant DNA which is incorporated into a vector, into an autonomously replicating plasmid or virus, or into the genomic DNA of a prokaryote or eukaryote, or which exists as a separate molecule (e.g., as a cDNA or a genomic or cDNA fragment produced by PCR or restriction enzyme digestion) independent of other sequences. It also includes a recombinant DNA which is part of a hybrid gene encoding additional polypeptide sequence.

A "ligand" is a compound that specifically binds to a target receptor.

A "receptor" is a compound that specifically binds to a ligand.

A ligand or a receptor (e.g., an antibody) "specifically binds to" or "is specifically immunoreactive with" a compound when the ligand or receptor functions in a binding reaction which is determinative of the presence of the compound in a sample of heterogeneous compounds. Thus, under designated assay (e.g., immunoassay) conditions, the ligand or receptor binds preferentially to a particular compound and does not bind in a significant amount to other compounds present in the sample. For example, a polynucleotide specifically binds under hybridization conditions to a compound polynucleotide comprising a complementary sequence; an antibody specifically binds under immunoassay conditions to an antigen bearing an epitope against which the antibody was raised. A variety of immunoassay formats may be used to select antibodies specifically immunoreactive with a particular protein. For example, solid-phase ELISA immunoassays are routinely used to select monoclonal antibodies specifically immunoreactive with a protein. See Harlow and Lane (1988, Antibodies, A Laboratory Manual, Cold Spring Harbor Publications, New York) for a description of immunoassay formats and conditions that can be used to determine specific immunoreactivity.

As used herein, the term "linkage" refers to a connection between two groups. The connection can be either covalent or non-covalent, including but not limited to ionic bonds, hydrogen bonding, and hydrophobic/hydrophilic interactions.

As used herein, the term "linker" refers to a molecule that joins two other molecules either covalently or noncovalently, e.g., through ionic or hydrogen bonds or van der Waals interactions, e.g., a nucleic acid molecule that hybridizes to one complementary sequence at the 5' end and to another complementary sequence at the 3' end, thus joining two non-complementary sequences.

"Malexpression" of a gene means expression of a gene in a cell of a patient afflicted with a disease or disorder, wherein the level of expression (including non-expression), the portion of the gene expressed, or the timing of the expression of the gene with regard to the cell cycle, differs from expression of the same gene in a cell of a patient not afflicted with the disease or disorder. It is understood that malexpression may cause or contribute to the disease or disorder, be a symptom of the disease or disorder, or both.

As used herein, the term "malignant" refers to having the properties of anaplasia, penetrance, such as into nearby areas or the vasculature, and metastasis.

The term "measuring the level of expression" or "determining the level of expression" as used herein refers to any measure or assay which can be used to correlate the results of the assay with the level of expression of a gene or protein of interest. Such assays include measuring the level of mRNA, protein levels, etc. and can be performed by assays such as northern and western blot analyses, binding assays, immunoblots, etc. The level of expression can include rates of expression and can be measured in terms of the actual amount of an mRNA or protein present. Such assays are coupled with processes or systems to store and process information and to help quantify levels, signals, etc. and to digitize the information for use in comparing levels.

The term "nasal administration" in all its grammatical forms refers to administration of at least one compound of the disclosure through the nasal mucous membrane to the bloodstream for systemic delivery of at least one compound of the disclosure. The advantages of nasal administration for delivery are that it does not require injection using a syringe and needle, it avoids necrosis that can accompany intramuscular administration of drugs, and trans-mucosal administration of a drug is highly amenable to self-administration.

The term "nucleic acid" typically refers to large polynucleotides. By "nucleic acid" is meant any nucleic acid, whether composed of deoxyribonucleosides or ribonucleosides, and whether composed of phosphodiester linkages or modified linkages such as phosphotriester, phosphoramidate, siloxane, carbonate, carboxymethylester, acetamidate, carbamate, thioether, bridged phosphoramidate, bridged methylene phosphonate, bridged phosphoramidate, bridged phosphoramidate, bridged methylene phosphonate, phosphorothioate, methylphosphonate, phosphorodithioate, bridged phosphorothioate or sulfone linkages, and combinations of such linkages. The term nucleic acid also specifically includes nucleic acids composed of bases other than the five biologically occurring bases (adenine, guanine, thymine, cytosine and uracil).

As used herein, the term "nucleic acid" encompasses RNA as well as single and double-stranded DNA and cDNA. Furthermore, the terms, "nucleic acid," "DNA," "RNA" and similar terms also include nucleic acid analogs, i.e. analogs having other than a phosphodiester backbone. For example, the so-called "peptide nucleic acids," which are known in the art and have peptide bonds instead of phosphodiester bonds in the backbone, are considered within the scope of the present disclosure. By "nucleic acid" is meant any nucleic acid, whether composed of deoxyribonucleosides or ribonucleosides, and whether composed of phosphodiester linkages or modified linkages such as phosphotriester, phosphoramidate, siloxane, carbonate, carboxymethylester, acetamidate, carbamate, thioether, bridged phosphoramidate, bridged methylene phosphonate, bridged phosphoramidate, bridged phosphoramidate, bridged methylene phosphonate, phosphorothioate, methylphosphonate, phosphorodithioate, bridged phosphorothioate or sulfone linkages, and combinations of such linkages. The term nucleic acid also specifically includes nucleic acids composed of bases other than the five biologically occurring bases (adenine, guanine, thymine, cytosine, and uracil). Conventional notation is used herein to describe polynucleotide sequences: the left-hand end of a single-stranded polynucleotide sequence is the 5'-end; the left-hand direction of a double-stranded polynucleotide sequence is referred to as the 5'-direction. The direction of 5' to 3' addition of nucleotides to nascent RNA transcripts is referred to as the transcription direction. The DNA strand having the same sequence as an mRNA is referred to as the "coding strand"; sequences on the DNA strand which are located 5' to a reference point on the DNA are referred to as "upstream sequences"; sequences on the DNA strand which are 3' to a reference point on the DNA are referred to as "downstream sequences."

The term "nucleic acid construct," as used herein, encompasses DNA and RNA sequences encoding the particular gene or gene fragment desired, whether obtained by genomic or synthetic methods.

Unless otherwise specified, a "nucleotide sequence encoding an amino acid sequence" includes all nucleotide sequences that are degenerate versions of each other and that encode the same amino acid sequence. Nucleotide sequences that encode proteins and RNA may include introns.

The term "oligonucleotide" typically refers to short polynucleotides, generally, no greater than about 50 nucleotides. It will be understood that when a nucleotide sequence is represented by a DNA sequence (i.e., A, T, G, C), this also includes an RNA sequence (i.e., A, U, G, C) in which "U" replaces "T."

By describing two polynucleotides as "operably linked" is meant that a single-stranded or double-stranded nucleic acid moiety comprises the two polynucleotides arranged within the nucleic acid moiety in such a manner that at least one of the two polynucleotides is able to exert a physiological effect by which it is characterized upon the other. By way of example, a promoter operably linked to the coding region of a gene is able to promote transcription of the coding region.

As used herein, "parenteral administration" of a pharmaceutical composition includes any route of administration characterized by physical breaching of a tissue of a subject and administration of the pharmaceutical composition through the breach in the tissue. Parenteral administration thus includes, but is not limited to, administration of a pharmaceutical composition by injection of the composition, by application of the composition through a surgical incision, by application of the composition through a tissue-penetrating non-surgical wound, and the like. In particular, parenteral administration is contemplated to include, but is not limited to, subcutaneous, intraperitoneal, intramuscular, intrasternal injection, and kidney dialytic infusion techniques.

The term "peptide" typically refers to short polypeptides or to peptides shorter than the full length native or mature protein.

The term "per application" as used herein refers to administration of a drug or compound to a subject.

The term "pharmaceutical composition" shall mean a composition comprising at least one active ingredient, whereby the composition is amenable to investigation for a specified, efficacious outcome in a mammal (for example, without limitation, a human). Those of ordinary skill in the art will understand and appreciate the techniques appropriate for determining whether an active ingredient has a desired efficacious outcome based upon the needs of the artisan.

As used herein, the term "pharmaceutically-acceptable carrier" means a chemical composition with which an appropriate compound or derivative can be combined and which, following the combination, can be used to administer the appropriate compound to a subject.

As used herein, the term "physiologically acceptable" ester or salt means an ester or salt form of the active ingredient which is compatible with any other ingredients of the pharmaceutical composition, which is not deleterious to the subject to which the composition is to be administered.

"Pharmaceutically acceptable" means physiologically tolerable, for either human or veterinary application.

As used herein, "pharmaceutical compositions" include formulations for human and veterinary use.

"Plurality" means at least two.

A "polynucleotide" means a single strand or parallel and anti-parallel strands of a nucleic acid. Thus, a polynucleotide may be either a single-stranded or a double-stranded nucleic acid.

"Polypeptide" refers to a polymer composed of amino acid residues, related naturally occurring structural variants, and synthetic non-naturally occurring analogs thereof linked via peptide bonds, related naturally occurring structural variants, and synthetic non-naturally occurring analogs thereof.

"Synthetic peptides or polypeptides" means a non-naturally occurring peptide or polypeptide. Synthetic peptides or polypeptides can be synthesized, for example, using an automated polypeptide synthesizer. Various solid phase peptide synthesis methods are known to those of skill in the art.

By "presensitization" is meant pre-administration of at least one innate immune system stimulator prior to challenge with an agent. This is sometimes referred to as induction of tolerance.

The term "prevent," as used herein, means to stop something from happening, or taking advance measures against something possible or probable from happening. In the context of medicine, "prevention" generally refers to action taken to decrease the chance of getting a disease or condition.

A "preventive" or "prophylactic" treatment is a treatment administered to a subject who does not exhibit signs, or exhibits only early signs, of a disease or disorder. A prophylactic or preventative treatment is administered for the purpose of decreasing the risk of developing pathology associated with developing the disease or disorder.

"Primer" refers to a polynucleotide that is capable of specifically hybridizing to a designated polynucleotide template and providing a point of initiation for synthesis of a complementary polynucleotide. Such synthesis occurs when the polynucleotide primer is placed under conditions in which synthesis is induced, i.e., in the presence of nucleotides, a complementary polynucleotide template, and an agent for polymerization such as DNA polymerase. A primer is typically single-stranded, but may be double-stranded. Primers are typically deoxyribonucleic acids, but a wide variety of synthetic and naturally occurring primers are useful for many applications. A primer is complementary to the template to which it is designed to hybridize to serve as a site for the initiation of synthesis, but need not reflect the exact sequence of the template. In such a case, specific hybridization of the primer to the template depends on the stringency of the hybridization conditions. Primers can be labeled with, e.g., chromogenic, radioactive, or fluorescent moieties and used as detectable moieties.

As used herein, the term "promoter/regulatory sequence" means a nucleic acid sequence which is required for expression of a gene product operably linked to the promoter/regulator sequence. In some instances, this sequence may be the core promoter sequence and in other instances, this sequence may also include an enhancer sequence and other regulatory elements which are required for expression of the gene product. The promoter/regulatory sequence may, for example, be one which expresses the gene product in a tissue specific manner.

A "constitutive" promoter is a promoter which drives expression of a gene to which it is operably linked, in a constant manner in a cell. By way of example, promoters which drive expression of cellular housekeeping genes are considered to be constitutive promoters.

An "inducible" promoter is a nucleotide sequence which, when operably linked with a polynucleotide which encodes or specifies a gene product, causes the gene product to be produced in a living cell substantially only when an inducer which corresponds to the promoter is present in the cell.

A "tissue-specific" promoter is a nucleotide sequence which, when operably linked with a polynucleotide which encodes or specifies a gene product, causes the gene product to be produced in a living cell substantially only if the cell is a cell of the tissue type corresponding to the promoter.

A "prophylactic" treatment is a treatment administered to a subject who does not exhibit signs of a disease or exhibits only early signs of the disease for the purpose of decreasing the risk of developing pathology associated with the disease.

As used herein, "protecting group" with respect to a terminal amino group refers to a terminal amino group of a peptide, which terminal amino group is coupled with any of various amino-terminal protecting groups traditionally employed in peptide synthesis. Such protecting groups include, for example, acyl protecting groups such as formyl, acetyl, benzoyl, trifluoroacetyl, succinyl, and methoxysuccinyl; aromatic urethane protecting groups such as benzyloxycarbonyl; and aliphatic urethane protecting groups, for example, tert-butoxycarbonyl or adamantyloxycarbonyl. See Gross and Mienhofer, eds., *The Peptides*, vol. 3, pp. 3-88 (Academic Press, New York, 1981) for suitable protecting groups.

As used herein, "protecting group" with respect to a terminal carboxy group refers to a terminal carboxyl group of a peptide, which terminal carboxyl group is coupled with any of various carboxyl-terminal protecting groups. Such protecting groups include, for example, tert-butyl, benzyl or other acceptable groups linked to the terminal carboxyl group through an ester or ether bond.

The term "protein" typically refers to large polypeptides. Conventional notation is used herein to portray polypeptide sequences: the left-hand end of a polypeptide sequence is the amino-terminus; the right-hand end of a polypeptide sequence is the carboxyl-terminus.

The term "protein regulatory pathway", as used herein, refers to both the upstream regulatory pathway which regulates a protein, as well as the downstream events which that protein regulates. Such regulation includes, but is not limited to, transcription, translation, levels, activity, posttranslational modification, and function of the protein of interest, as well as the downstream events which the protein regulates.

The terms "protein pathway" and "protein regulatory pathway" are used interchangeably herein.

As used herein, the term "purified" and like terms relate to an enrichment of a molecule or compound relative to other components normally associated with the molecule or compound in a native environment. The term "purified" does not necessarily indicate that complete purity of the particular molecule has been achieved during the process. A "highly purified" compound as used herein refers to a compound that is greater than 90% pure. A "significant detectable level" is an amount of contaminate that would be visible in the presented data and would need to be addressed/explained during analysis of the forensic evidence.

"Recombinant polynucleotide" refers to a polynucleotide having sequences that are not naturally joined together. An amplified or assembled recombinant polynucleotide may be included in a suitable vector, and the vector can be used to transform a suitable host cell.

A recombinant polynucleotide may serve a non-coding function (e.g., promoter, origin of replication, ribosome-binding site, etc.) as well.

A host cell that comprises a recombinant polynucleotide is referred to as a "recombinant host cell." A gene which is expressed in a recombinant host cell wherein the gene comprises a recombinant polynucleotide, produces a "recombinant polypeptide."

A "recombinant polypeptide" is one which is produced upon expression of a recombinant polynucleotide.

A "receptor" is a compound that specifically binds to a ligand.

A "ligand" is a compound that specifically binds to a target receptor.

A "recombinant cell" is a cell that comprises a transgene. Such a cell may be a eukaryotic or a prokaryotic cell. Also, the transgenic cell encompasses, but is not limited to, an embryonic stem cell comprising the transgene, a cell obtained from a chimeric mammal derived from a transgenic embryonic stem cell where the cell comprises the transgene, a cell obtained from a transgenic mammal, or fetal or placental tissue thereof, and a prokaryotic cell comprising the transgene.

The term "regulate" refers to either stimulating or inhibiting a function or activity of interest.

As used herein, the term "reporter gene" means a gene, the expression of which can be detected using a known method. By way of example, the *Escherichia coli* lacZ gene may be used as a reporter gene in a medium because expression of the lacZ gene can be detected using known methods by adding the chromogenic substrate o-nitrophenyl-β-galactoside to the medium (Gerhardt et al., eds., 1994, *Methods for General and Molecular Bacteriology*, American Society for Microbiology, Washington, DC, p. 574).

A "sample," as used herein, refers preferably to a biological sample from a subject for which an assay or other use is needed, including, but not limited to, normal tissue samples, diseased tissue samples, sputum, mucus, phlegm, biopsies, cerebrospinal fluid, blood, serum, plasma, other blood components, gastric aspirates, throat swabs, pleural effusion, peritoneal fluid, follicular fluid, ascites, skin, hair, tissue, blood, plasma, cells, saliva, sweat, tears, semen, stools, Pap smears, and urine. A sample can also be any other source of material obtained from a subject that contains cells, tissues, or fluid of interest. A sample can also be obtained from cell or tissue culture.

As used herein, the term "secondary antibody" refers to an antibody that binds to the constant region of another antibody (the primary antibody).

By the term "signal sequence" is meant a polynucleotide sequence which encodes a peptide that directs the path a polypeptide takes within a cell, i.e., it directs the cellular processing of a polypeptide in a cell, including, but not limited to, eventual secretion of a polypeptide from a cell. A signal sequence is a sequence of amino acids which are typically, but not exclusively, found at the amino terminus of a polypeptide which targets the synthesis of the polypeptide to the endoplasmic reticulum. In some instances, the signal peptide is proteolytically removed from the polypeptide and is thus absent from the mature protein.

By "small interfering RNAs (siRNAs)" is meant, inter alia, an isolated dsRNA molecule comprised of both a sense and an anti-sense strand. In one aspect, it is greater than 10 nucleotides in length. siRNA also refers to a single transcript which has both the sense and complementary antisense sequences from the target gene, e.g., a hairpin. siRNA further includes any form of dsRNA (proteolytically cleaved products of larger dsRNA, partially purified RNA, essentially pure RNA, synthetic RNA, recombinantly produced RNA) as well as altered RNA that differs from naturally occurring RNA by the addition, deletion, substitution, and/or alteration of one or more nucleotides.

As used herein, the term "solid support" relates to a solvent insoluble substrate that is capable of forming linkages (preferably covalent bonds) with various compounds. The support can be either biological in nature, such as, without limitation, a cell or bacteriophage particle, or synthetic, such as, without limitation, an acrylamide derivative, agarose, cellulose, nylon, silica, or magnetized particles.

By the term "specifically binds to", as used herein, is meant when a compound or ligand functions in a binding reaction or assay conditions which is determinative of the presence of the compound in a sample of heterogeneous compounds.

The term "standard," as used herein, refers to something used for comparison. For example, it can be a known standard agent or compound which is administered and used for comparing results when administering a test compound, or it can be a standard parameter or function which is measured to obtain a control value when measuring an effect of an agent or compound on a parameter or function. Standard can also refer to an "internal standard", such as an agent or compound which is added at known amounts to a sample and is useful in determining such things as purification or recovery rates when a sample is processed or subjected to purification or extraction procedures before a marker of interest is measured. Internal standards are often a purified marker of interest which has been labeled, such as with a radioactive isotope, allowing it to be distinguished from an endogenous marker.

A "subject" of analysis, diagnosis, or treatment is an animal. Such animals include mammals, preferably a human.

As used herein, a "subject in need thereof" is a patient, animal, mammal, or human, who will benefit from the method of this disclosure.

As used herein, a "substantially homologous amino acid sequences" includes those amino acid sequences which have at least about 95% homology, preferably at least about 96% homology, more preferably at least about 97% homology, even more preferably at least about 98% homology, and most preferably at least about 99% or more homology to an amino acid sequence of a reference antibody chain. Amino acid sequence similarity or identity can be computed by using the BLASTP and TBLASTN programs which employ the BLAST (basic local alignment search tool) 2.0.14 algorithm. The default settings used for these programs are suitable for identifying substantially similar amino acid sequences for purposes of the present disclosure.

"Substantially homologous nucleic acid sequence" means a nucleic acid sequence corresponding to a reference nucleic acid sequence wherein the corresponding sequence encodes a peptide having substantially the same structure and function as the peptide encoded by the reference nucleic acid sequence; e.g., where only changes in amino acids not significantly affecting the peptide function occur. Preferably, the substantially identical nucleic acid sequence encodes the peptide encoded by the reference nucleic acid sequence. The percentage of identity between the substantially similar nucleic acid sequence and the reference nucleic acid sequence is at least about 50%, 65%, 75%, 85%, 95%, 99% or more. Substantial identity of nucleic acid sequences can be determined by comparing the sequence identity of two sequences, for example by physical/chemical methods (i.e., hybridization) or by sequence alignment via computer algorithm. Suitable nucleic acid hybridization conditions to determine if a nucleotide sequence is substantially similar to a reference nucleotide sequence are: 7% sodium dodecyl sulfate SDS, 0.5 M $NaPO_4$, 1 mM EDTA at 50° C. with washing in 2× standard saline citrate (SSC), 0.1% SDS at 50° C.; preferably in 7% (SDS), 0.5 M $NaPO_4$, 1 mM EDTA at 50° C. with washing in 1×SSC, 0.1% SDS at 50° C.; preferably 7% SDS, 0.5 M $NaPO_4$, 1 mM EDTA at 50° C. with washing in 0.5×SSC, 0.1% SDS at 50° C.; and more preferably in 7% SDS, 0.5 M $NaPO_4$, 1 mM EDTA at 50° C. with washing in 0.1×SSC, 0.1% SDS at 65° C. Suitable computer algorithms to determine substantial similarity between two nucleic acid sequences include, GCS program package (Devereux et al., 1984 Nucl. Acids Res. 12:387), and the BLASTN or FASTA programs (Altschul et al., 1990 Proc. Natl. Acad. Sci. USA. 1990 87:14:5509-13; Altschul et al., J. Mol. Biol. 1990 215:3:403-10; Altschul et al., 1997 Nucleic Acids Res. 25:3389-3402). The default settings provided with these programs are suitable for determining substantial similarity of nucleic acid sequences for purposes of the present disclosure.

The term "substantially pure" describes a compound, e.g., a protein or polypeptide which has been separated from components which naturally accompany it. Typically, a compound is substantially pure when at least 10%, more preferably at least 20%, more preferably at least 50%, more preferably at least 60%, more preferably at least 75%, more preferably at least 90%, and most preferably at least 99% of the total material (by volume, by wet or dry weight, or by mole percent or mole fraction) in a sample is the compound of interest. Purity can be measured by any appropriate method, e.g., in the case of polypeptides by column chromatography, gel electrophoresis, or HPLC analysis. A compound, e.g., a protein, is also substantially purified when it is essentially free of naturally associated components or when it is separated from the native contaminants which accompany it in its natural state.

The term "symptom," as used herein, refers to any morbid phenomenon or departure from the normal in structure, function, or sensation, experienced by the patient and indicative of disease. In contrast, a "sign" is objective evidence of disease. For example, a bloody nose is a sign. It is evident to the patient, doctor, nurse and other observers.

A "therapeutic" treatment is a treatment administered to a subject who exhibits signs of pathology for the purpose of diminishing or eliminating those signs.

A "therapeutically effective amount" of a compound is that amount of compound which is sufficient to provide a beneficial effect to the subject to which the compound is administered.

As used herein, the term "transgene" means an exogenous nucleic acid sequence comprising a nucleic acid which encodes a promoter/regulatory sequence operably linked to nucleic acid which encodes an amino acid sequence, which exogenous nucleic acid is encoded by a transgenic mammal.

As used herein, the term "transgenic mammal" means a mammal, the germ cells of which comprise an exogenous nucleic acid.

As used herein, a "transgenic cell" is any cell that comprises a nucleic acid sequence that has been introduced into the cell in a manner that allows expression of a gene encoded by the introduced nucleic acid sequence.

The term to "treat," as used herein, means reducing the frequency with which symptoms are experienced by a patient or subject or administering an agent or compound to reduce the frequency with which symptoms are experienced.

A "prophylactic" treatment is a treatment administered to a subject who does not exhibit signs of a disease or exhibits only early signs of the disease for the purpose of decreasing the risk of developing pathology associated with the disease.

A "variant", as described herein, refers to a segment of DNA that differs from the reference DNA. A "marker" or a "polymorphic marker", as defined herein, is a variant. Alleles that differ from the reference are referred to as "variant" alleles.

A "vector" is a composition of matter which comprises an isolated nucleic acid and which can be used to deliver the isolated nucleic acid to the interior of a cell. Numerous vectors are known in the art including, but not limited to, linear polynucleotides, polynucleotides associated with ionic or amphiphilic compounds, plasmids, and viruses. Thus, the term "vector" includes an autonomously replicating plasmid or a virus. The term should also be construed to include non-plasmid and non-viral compounds which facilitate transfer or delivery of nucleic acid to cells, such as, for example, polylysine compounds, liposomes, and the like. Examples of viral vectors include, but are not limited to, adenoviral vectors, adeno-associated virus vectors, retroviral vectors, recombinant viral vectors, and the like. Examples of non-viral vectors include, but are not limited to, liposomes, polyamine derivatives of DNA and the like.

"Expression vector" refers to a vector comprising a recombinant polynucleotide comprising expression control sequences operatively linked to a nucleotide sequence to be expressed. An expression vector comprises sufficient cis-acting elements for expression; other elements for expression can be supplied by the host cell or in an in vitro expression system. Expression vectors include all those known in the art, such as cosmids, plasmids (e.g., naked or contained in liposomes) and viruses that incorporate the recombinant polynucleotide.

Embodiments

Previous work showed that many but not all melanomas are inherently sensitive to chemotherapy but become resistant as a consequence of changes in interactions with surrounding extracellular matrix (ECM). These tumors become resistant to chemotherapy when the ECM within the tumor is degraded and integrins are not engaged and signaling.

The present disclosure encompasses compositions and methods useful for blocking or inhibiting LRP1 function, expression, levels and synthesis to overcome its role regulating myelination. In one aspect, LRP1 is inhibited using an antibody directed against it. In one aspect, the antibody is a monoclonal antibody. In one aspect, the monoclonal antibody. In one aspect, LRP1 is inhibited using siRNA directed against it. In one aspect, the siRNA targets a sequence comprising one or more of SEQ ID NOs: 1-8. For example, the siRNA can target one or more sequences selected from the group consisting of SEQ ID NOs: 1-4 or one or more sequences selected from the group consisting of SEQ ID NOs: 5-8. The siRNA can target a sequence comprising SEQ ID NO:1, SEQ ID NO:2, SEQ ID NO:3, SEQ ID NO: 4, SEQ ID NO:5, SEQ ID NO:6, SEQ ID NO:7, or SEQ ID NO: 8. One of ordinary skill in the art will appreciate that other types of molecules that can inhibit RLP1 expression, synthesis, levels, and activity are encompassed by the disclosure, including antisense oligonucleotides and aptamers.

One of ordinary skill in the art will appreciate that the sequences can be modified with conservative amino acid changes, including, insertions, deletions, and substitutions, and that the valency could be altered as well, as long as the resulting multimer/multimeric complex remains effective. Amino acid changes (fragments and homologs) can be made independently in each fibronectin and in COMP. One of ordinary skill in the art will appreciate that C-terminal groups other than His6 can be used. One of skill in the art will also realize that the pentameric, or other valency, complex can be linked in different ways.

In another aspect, the administration of a compound of the disclosure can be performed at the same time other therapies are being administered. One of ordinary skill in the art will appreciate that numerous techniques are known for determining the best routes, dosages, and timing of administration, as well as how many times administration should occur. The present disclosure encompasses compounds other than antibodies.

The present disclosure further provides compositions and methods useful for precision, personalized medicine. In one embodiment, the present disclosure provides compositions and methods useful for selecting a subject who will be responsive to treatment.

Various types of molecules are encompassed within the methods of the disclosure and are useful for inhibiting the effects of LRP1. The inhibition may be direct or indirect. For example, useful molecules for inhibiting LRP1 include, but are not limited to, RNAi/siRNA, antisense oligonucleotides, antibodies, aptamers, and other agents and compounds. The compounds of the disclosure may regulate LRP1 by regulating processes and functions including, but not limited to, gene expression of LRP1, translation of LRP1, protein levels of LRP1, protein degradation of LRP1, binding of LRP1 with other molecules, as well as both downstream and upstream pathways regulating LRP1 and its functions. By regulating LRP1 is meant regulating LRP1 synthesis, levels, function/activity, binding, and any upstream or downstream pathways regulating LRP1 and its functions.

In one embodiment, the antibody directed against is selected from the group consisting of a single chain antibody, a monoclonal antibody, a bi-specific antibody, a chimeric antibody, a synthetic antibody, a polyclonal antibody, or a humanized antibody, or active fragments or homologs thereof.

In one aspect, a compound of the disclosure can be administered by a route selected from, including, but not limited to, intravenously, intrathecally, locally, intramuscularly, topically, orally, intra-arterially, parenterally, etc. One of ordinary skill in the art can determine how often to administer the compound, the dose to be used, and what combination of other agents it can be administered with such as chemotherapeutic agents and/or inhibitors of LRP1 levels or expression. One of ordinary skill in the art can also determine if all compounds should be administered simultaneously or not.

In one embodiment, a compound dosage of about 0.1 mg/kg to about 100 mg/kg can be administered to a subject in need thereof, including whole numbers between 0.1 and 100 and fractions thereof. In one aspect, a multimeric peptide construct dosage of about 1.0 mg/kg to about 75 mg/kg can be administered to a subject. In another aspect, a compound dosage of about 5.0 mg/kg to about 50 mg/kg can be administered to a subject. In yet another aspect, a compound dosage of about 10 mg/kg to about 25 mg/kg can be administered to a subject. In a further aspect, a compound dosage of about 15 mg/kg to about 20 mg/kg can be administered to a subject. Numerical ranges recited herein by endpoints include all numbers and fractions subsumed within that range (e.g., 1 to 5 includes 1, 1.5, 2, 2.75, 3, 3.90, 4, and 5). It is also to be understood that all numbers and fractions thereof are presumed to be modified by the term "about."

In one embodiment, a unit dose of a compound of the disclosure can be administered. Other therapeutic agents of the disclosure can also be administered as unit doses. Kits can be provided with unit doses in a container or syringe or amounts that one of ordinary skill in the art can administer based on a dose per weight, etc.

In one embodiment, a compound of the disclosure is administered at least once a day, or once a week, or once month. In one embodiment, a compound of the disclosure is administered at least twice a day, or twice a week, or twice a month.

The disclosure further includes isolated nucleic acids comprising sequences encoding peptides of the disclosure.

In one embodiment, the useful peptides of the disclosure are used and can be modified by adding additional amino acids or substituting amino acids during synthesis.

In one embodiment, the imaging agent is coupled to an antibody directed against LRP1.

Optionally the peptide ligands are modified with conservative amino acid substitutions or additional standard or non-standards are added to enhance distribution or time before degradation.

Antibodies

Antibodies refer to polypeptides substantially encoded by an immunoglobulin gene or immunoglobulin genes, or fragments thereof, which specifically bind and recognize an analyte (antigen). The recognized immunoglobulin genes include the kappa, lambda, alpha, gamma, delta, epsilon and mu constant region genes, as well as the myriad immunoglobulin variable region genes. Light chains are classified as either kappa or lambda. Heavy chains are classified as gamma, mu, alpha, delta, or epsilon, which in turn define the immunoglobulin classes, IgG, IgM, IgA, IgD and IgE, respectively.

An exemplary immunoglobulin (antibody) structural unit comprises a tetramer. Each tetramer is composed of two identical pairs of polypeptide chains, each pair having one "light" (about 25 kD) and one "heavy" chain (about 50-70 kD). The N-terminus of each chain defines a variable region of about 100 to 110 or more amino acids primarily responsible for antigen recognition. The terms variable light chain ($V_L$) and variable heavy chain ($V_H$) refer to these light and heavy chains respectively.

A variety of methods for producing polyclonal and monoclonal antibodies are known in the art. See, e.g., Goding, MONOCLONAL ANTIBODIES; PRINCIPLES AND PRACTICE, Academic Press, 2nd Edition (1986); and Harlow & Lane. A monoclonal antibody directed against or reactive with, for example, human cells expressing a desired antigen is obtained by using combinations of immunogens to immunize mice and screening hybridoma supernatant against cells which express the desired antigen or by a screening assay designed to be specific for monoclonal antibodies directed against the antigen of interest. Useful cell lines for screening for the antibodies of this disclosure are readily available or obtained. Such cells include the Burkitt's lymphoma cell lines Daudi, and Raji.

Recombinant DNA methodologies can be used to synthesize antibodies of this disclosure. For example, an antibody portion of an immunotoxin for use in humans is a "humanized" antibody against a cell antigen which contains murine complementarity-determining regions (CDRs) combined with human variable region frameworks and human constant regions.

Humanized (chimeric) antibodies are immunoglobulin molecules comprising a human and non-human portion. More specifically, the antigen combining region (or variable region) of a humanized chimeric antibody is derived from a non-human source (e.g., murine) and the constant region of the chimeric antibody (which confers biological effector function to the immunoglobulin) is derived from a human source. The humanized chimeric antibody should have the antigen binding specificity of the non-human antibody molecule and the effector function conferred by the human antibody molecule. A large number of methods of generating chimeric antibodies are well known to those of skill in the art (see, e.g., U.S. Pat. Nos. 5,502,167, 5,500,362, 5,491,088, 5,482,856, 5,472,693, 5,354,847, 5,292,867, 5,231,026, 5,204,244, 5,202,238, 5,169,939, 5,081,235, 5,075,431, and 4,975,369). Detailed methods for preparation of chimeric (humanized) antibodies can be found in U.S. Pat. No. 5,482,856.

In another embodiment, this disclosure provides for fully human antibodies. Human antibodies consist entirely of characteristically human polypeptide sequences. The human antibodies of this disclosure can be produced in using a wide variety of methods (see, e.g., Larrick et al, U.S. Pat. No. 5,001,065, for review).

The antibody moieties of this disclosure can be single chain antibodies. In one embodiment, techniques described for the production of single-chain antibodies (U.S. Pat. No. 4,946,778, incorporated by reference herein in its entirety) are adapted to produce protein-specific single-chain antibodies. In another embodiment, the techniques described for the construction of Fab expression libraries (Huse et al., 1989*, Science* 246:1275-1281) are utilized to allow rapid and easy identification of monoclonal Fab fragments possessing the desired specificity for specific antigens, proteins, derivatives, or analogs of the disclosure.

Antibodies directed against proteins, polypeptides, or peptide fragments thereof of the disclosure may be generated using methods that are well known in the art. For instance, U.S. patent application Ser. No. 07/481,491, which is incorporated by reference herein in its entirety, discloses methods of raising antibodies to peptides. For the production of antibodies, various host animals, including but not limited to rabbits, mice, and rats, can be immunized by injection with a polypeptide or peptide fragment thereof. To increase the immunological response, various adjuvants may be used depending on the host species, including but not limited to Freund's (complete and incomplete), mineral gels such as aluminum hydroxide, surface active substances such as lysolecithin, pluronic polyols, polyanions, peptides, oil emulsions, keyhole limpet hemocyanins, dinitrophenol, and potentially useful human adjuvants such as BCG (bacille Calmette-Guerin) and *Corynebacterium parvum.*

In one embodiment, antibodies, or antisera, directed against LRP1 or a homolog or fragment thereof, are useful for blocking the activity of LRP1, including its ability to interact with other molecules or cells.

Fragments of LRP1 may be generated and antibodies prepared against the fragments. Assays are provided herein to determine whether an antibody directed against LRP1, or a fragment thereof, have the ability to detect LRP1, to inhibit LRP1 activity, or regulate LRP1 function.

In one embodiment, techniques described for the production of single-chain antibodies (U.S. Pat. No. 4,946,778, incorporated by reference herein in its entirety) are adapted to produce protein-specific single-chain antibodies. In another embodiment, the techniques described for the construction of Fab expression libraries (Huse et al., 1989, *Science* 246:1275-1281) are utilized to allow rapid and easy identification of monoclonal Fab fragments possessing the desired specificity for specific antigens, proteins, derivatives, or analogs of the disclosure.

Antibody fragments which contain the idiotype of the antibody molecule can be generated by known techniques. For example, such fragments include but are not limited to: the $F(ab')_2$ fragment which can be produced by pepsin digestion of the antibody molecule; the Fab' fragments which can be generated by reducing the disulfide bridges of the $F(ab')_2$ fragment; the Fab fragments which can be generated by treating the antibody molecule with papain and a reducing agent; and Fv fragments.

The generation of polyclonal antibodies is accomplished by inoculating the desired animal with the antigen and isolating antibodies which specifically bind the antigen therefrom.

Monoclonal antibodies directed against full length or peptide fragments of a protein or peptide may be prepared using any well-known monoclonal antibody preparation procedures, such as those described, for example, in Harlow et al. (1988, In: Antibodies, A Laboratory Manual, Cold Spring Harbor, NY) and in Tuszynski et al. (1988, Blood, 72:109-115). Quantities of the desired peptide may also be synthesized using chemical synthesis technology. Alternatively, DNA encoding the desired peptide may be cloned and expressed from an appropriate promoter sequence in cells suitable for the generation of large quantities of peptide. Monoclonal antibodies directed against the peptide are generated from mice immunized with the peptide using standard procedures as referenced herein.

A nucleic acid encoding the monoclonal antibody obtained using the procedures described herein may be cloned and sequenced using technology which is available in the art, and is described, for example, in Wright et al. (1992, Critical Rev. in Immunol. 12 (3,4): 125-168) and the references cited therein. Further, the antibody of the disclosure may be "humanized" using the technology described in Wright et al., (supra) and in the references cited therein, and in Gu et al. (1997, Thrombosis and Hematocyst 77 (4): 755-759).

To generate a phage antibody library, a cDNA library is first obtained from mRNA which is isolated from cells, e.g., the hybridoma, which express the desired protein to be expressed on the phage surface, e.g., the desired antibody. cDNA copies of the mRNA are produced using reverse transcriptase. cDNA which specifies immunoglobulin fragments are obtained by PCR and the resulting DNA is cloned into a suitable bacteriophage vector to generate a bacteriophage DNA library comprising DNA specifying immunoglobulin genes. The procedures for making a bacteriophage library comprising heterologous DNA are well known in the art and are described, for example, in Sambrook et al. (1989, Molecular Cloning: A Laboratory Manual, Cold Spring Harbor, NY).

Bacteriophages which encode the desired antibody, may be engineered such that the protein is displayed on the surface thereof in such a manner that it is available for binding to its corresponding binding protein, e.g., the antigen against which the antibody is directed. Thus, when bacteriophage which express a specific antibody are incubated in the presence of a cell which expresses the corresponding antigen, the bacteriophage will bind to the cell. Bacteriophages which do not express the antibody will not bind to the cell. Such panning techniques are well known in the art.

Processes such as those described above, have been developed for the production of human antibodies using M13 bacteriophage display (Burton et al., 1994, Adv. Immunol. 57:191-280). Essentially, a cDNA library is generated from mRNA obtained from a population of antibody-producing cells. The mRNA encodes rearranged immunoglobulin genes and thus, the cDNA encodes the same. Amplified cDNA is cloned into M13 expression vectors creating a library of phage which express human Fab fragments on their surface. Phages which display the antibody of interest are selected by antigen binding and are propagated in bacteria to produce soluble human Fab immunoglobulin. Thus, in contrast to conventional monoclonal antibody synthesis, this procedure immortalizes DNA encoding human immunoglobulin rather than cells which express human immunoglobulin.

The procedures just presented describe the generation of phage which encode the Fab portion of an antibody molecule. However, the disclosure should not be construed to be limited solely to the generation of phage encoding Fab antibodies. Rather, phages which encode single chain antibodies (scFv/phage antibody libraries) are also included in the disclosure. Fab molecules comprise the entire Ig light chain, that is, they comprise both the variable and constant region of the light chain, but include only the variable region and first constant region domain (CH1) of the heavy chain. Single chain antibody molecules comprise a single chain of protein comprising the Ig Fv fragment. An Ig Fv fragment includes only the variable regions of the heavy and light chains of the antibody, having no constant region contained therein. Phage libraries comprising scFv DNA may be generated following the procedures described in Marks et al., 1991, J. Mol. Biol. 222:581-597. Panning of phage so generated for the isolation of a desired antibody is conducted in a manner similar to that described for phage libraries comprising Fab DNA.

The disclosure should also be construed to include synthetic phage display libraries in which the heavy and light chain variable regions may be synthesized such that they include nearly all possible specificities (Barbas, 1995, Nature Medicine 1:837-839; de Kruif et al. 1995, J. Mol. Biol. 248:97-105).

In the production of antibodies, screening for the desired antibody can be accomplished by techniques known in the art, e.g., ELISA (enzyme-linked immunosorbent assay). Antibodies generated in accordance with the present disclosure may include, but are not limited to, polyclonal, monoclonal, chimeric (i.e., "humanized"), and single chain (recombinant) antibodies, Fab fragments, and fragments produced by a Fab expression library.

The peptides of the present disclosure may be readily prepared by standard, well-established techniques, such as solid-phase peptide synthesis (SPPS) as described by Stewart et al. in *Solid Phase Peptide Synthesis,* 2nd Edition, 1984, Pierce Chemical Company, Rockford, Illinois; and as described by Bodanszky and Bodanszky in *The Practice of Peptide Synthesis,* 1984, Springer-Verlag, New York. At the outset, a suitably protected amino acid residue is attached through its carboxyl group to a derivatized, insoluble polymeric support, such as cross-linked polystyrene or polyamide resin. "Suitably protected" refers to the presence of protecting groups on both the α-amino group of the amino acid, and on any side chain functional groups. Side chain protecting groups are generally stable to the solvents, reagents and reaction conditions used throughout the synthesis, and are removable under conditions that will not affect the final peptide product. Stepwise synthesis of the oligopeptide is carried out by the removal of the N-protecting group from the initial amino acid, and couple thereto of the carboxyl end of the next amino acid in the sequence of the desired peptide. This amino acid is also suitably protected. The carboxyl of the incoming amino acid can be activated to react with the N-terminus of the support-bound amino acid by formation into a reactive group such as formation into a carbodiimide, a symmetric acid anhydride or an "active ester" group such as hydroxybenzotriazole or pentafluorophenly esters.

Examples of solid phase peptide synthesis methods include the BOC method that utilized tert-butyloxcarbonyl as the α-amino protecting group, and the FMOC method which utilizes 9-fluorenylmethyloxcarbonyl to protect the α-amino of the amino acid residues, both methods of which are well-known by those of skill in the art.

To ensure that the proteins or peptides obtained from either chemical or biological synthetic techniques is the desired peptide, analysis of the peptide composition should be conducted. Such amino acid composition analysis may be conducted using high resolution mass spectrometry to determine the molecular weight of the peptide. Alternatively, or additionally, the amino acid content of the peptide can be confirmed by hydrolyzing the peptide in aqueous acid, and separating, identifying and quantifying the components of the mixture using HPLC, or an amino acid analyzer. Protein sequenators, which sequentially degrade the peptide and identify the amino acids in order, may also be used to determine definitely the sequence of the peptide.

Prior to its use, the peptide can be purified to remove contaminants. In this regard, it will be appreciated that the peptide will be purified to meet the standards set out by the appropriate regulatory agencies. Any one of a number of a conventional purification procedures may be used to attain the required level of purity including, for example, reversed-phase high-pressure liquid chromatography (HPLC) using an alkylated silica column such as $C_4$-, $C_8$- or $C_{18}$-silica. A gradient mobile phase of increasing organic content is generally used to achieve purification, for example, acetonitrile in an aqueous buffer, usually containing a small amount of trifluoroacetic acid. Ion-exchange chromatography can be also used to separate peptides based on their charge.

Substantially pure peptide obtained as described herein may be purified by following known procedures for protein purification, wherein an immunological, enzymatic or other assay is used to monitor purification at each stage in the procedure. Protein purification methods are well known in the art, and are described, for example in Deutscher et al. (ed., 1990, *Guide to Protein Purification*, Harcourt Brace Jovanovich, San Diego).

Peptide Modification and Preparation

Peptide preparation is described in the Examples. It will be appreciated, of course, that the proteins or peptides of the disclosure may incorporate amino acid residues which are modified without affecting activity. For example, the termini may be derivatized to include blocking groups, i.e. chemical substituents suitable to protect and/or stabilize the N- and C-termini from "undesirable degradation", a term meant to encompass any type of enzymatic, chemical or biochemical breakdown of the compound at its termini which is likely to affect the function of the compound, i.e. sequential degradation of the compound at a terminal end thereof.

Blocking groups include protecting groups conventionally used in the art of peptide chemistry which will not adversely affect the in vivo activities of the peptide. For example, suitable N-terminal blocking groups can be introduced by alkylation or acylation of the N-terminus. Examples of suitable N-terminal blocking groups include $C_1$-$C_5$ branched or unbranched alkyl groups, acyl groups such as formyl and acetyl groups, as well as substituted forms thereof, such as the acetamidomethyl (Acm) group. Desamino analogs of amino acids are also useful N-terminal blocking groups, and can either be coupled to the N-terminus of the peptide or used in place of the N-terminal reside. Suitable C-terminal blocking groups, in which the carboxyl group of the C-terminus is either incorporated or not, include esters, ketones or amides. Ester or ketone-forming alkyl groups, particularly lower alkyl groups such as methyl, ethyl and propyl, and amide-forming amino groups such as primary amines (—$NH_2$), and mono- and di-alkylamino groups such as methylamino, ethylamino, dimethylamino, diethylamino, methylethylamino and the like are examples of C-terminal blocking groups. Descarboxylated amino acid analogues such as agmatine are also useful C-terminal blocking groups and can be either coupled to the peptide's C-terminal residue or used in place of it. Further, it will be appreciated that the free amino and carboxyl groups at the termini can be removed altogether from the peptide to yield desamino and descarboxylated forms thereof without effect on peptide activity.

Acid addition salts of the present disclosure are also contemplated as functional equivalents. Thus, a peptide in accordance with the present disclosure treated with an inorganic acid such as hydrochloric, hydrobromic, sulfuric, nitric, phosphoric, and the like, or an organic acid such as an acetic, propionic, glycolic, pyruvic, oxalic, malic, malonic, succinic, maleic, fumaric, tataric, citric, benzoic, cinnamie, mandelic, methanesulfonic, ethanesulfonic, p-toluenesulfonic, salicyclic and the like, to provide a water soluble salt of the peptide is suitable for use in the disclosure.

Modifications (which do not normally alter primary sequence) include in vivo, or in vitro chemical derivatization of polypeptides, e.g., acetylation, or carboxylation. Also included are modifications of glycosylation, e.g., those made by modifying the glycosylation patterns of a polypeptide during its synthesis and processing or in further processing steps; e.g., by exposing the polypeptide to enzymes which affect glycosylation, e.g., mammalian glycosylating or deglycosylating enzymes. Also embraced are sequences which have phosphorylated amino acid residues, e.g., phosphotyrosine, phosphoserine, or phosphothreonine.

Also included are polypeptides which have been modified using ordinary molecular biological techniques so as to improve their resistance to proteolytic degradation or to optimize solubility properties or to render them more suitable as a therapeutic agent. Analogs of such polypeptides include those containing residues other than naturally occurring L-amino acids, e.g., D-amino acids or non-naturally occurring or non-standard synthetic amino acids. The peptides of the disclosure are not limited to products of any of the specific exemplary processes listed herein.

The disclosure includes the use of beta-alanine (also referred to as β-alanine, β-Ala, bA, and βA, having the structure:

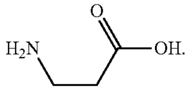

beta alanine

Sequences are provided herein which use the symbol "βA", but in the Sequence Listing submitted herewith "βA" is provided as "Xaa" and reference in the text of the Sequence Listing indicates that Xaa is beta alanine.

Peptides useful in the present disclosure, such as standards, or modifications for analysis, may be readily prepared by standard, well-established techniques, such as solid-phase peptide synthesis (SPPS) as described by Stewart et al. in *Solid Phase Peptide Synthesis,* 2nd Edition, 1984, Pierce Chemical Company, Rockford, Illinois; and as described by Bodanszky and Bodanszky in *The Practice of Peptide Synthesis,* 1984, Springer-Verlag, New York. At the outset, a suitably protected amino acid residue is attached through its carboxyl group to a derivatized, insoluble polymeric support, such as cross-linked polystyrene or polyamide resin. "Suitably protected" refers to the presence of protecting groups on both the α-amino group of the amino acid, and on any side chain functional groups. Side chain protecting groups are generally stable to the solvents, reagents and reaction conditions used throughout the synthesis, and are removable under conditions which will not affect the final peptide product. Stepwise synthesis of the oligopeptide is carried out by the removal of the N-protecting group from the initial amino acid, and couple thereto of the carboxyl end of the next amino acid in the sequence of the desired peptide. This amino acid is also suitably protected. The carboxyl of the incoming amino acid can be activated to react with the N-terminus of the support-bound amino acid by formation into a reactive group such as formation into a carbodiimide, a symmetric acid anhydride or an "active ester" group such as hydroxybenzotriazole or pentafluorophenly esters.

Examples of solid phase peptide synthesis methods include the BOC method which utilized tert-butyloxcarbonyl as the α-amino protecting group, and the FMOC method which utilizes 9-fluorenylmethyloxcarbonyl to protect the α-amino of the amino acid residues, both methods of which are well-known by those of skill in the art.

Incorporation of N- and/or C-blocking groups can also be achieved using protocols conventional to solid phase peptide synthesis methods. For incorporation of C-terminal blocking groups, for example, synthesis of the desired peptide is typically performed using, as solid phase, a supporting resin that has been chemically modified so that cleavage from the resin results in a peptide having the desired C-terminal blocking group. To provide peptides in which the C-terminus bears a primary amino blocking group, for instance, synthesis is performed using a p-methylbenzhydrylamine (MBHA) resin so that, when peptide synthesis is completed, treatment with hydrofluoric acid releases the desired C-terminally amidated peptide. Similarly, incorporation of an N-methylamine blocking group at the C-terminus is achieved using N-methylaminoethyl-derivatized DVB, resin, which upon HF treatment releases a peptide bearing an N-methylamidated C-terminus. Blockage of the C-terminus by esterification can also be achieved using conventional procedures. This entails use of resin/blocking group combination that permits release of side-chain peptide from the resin, to allow for subsequent reaction with the desired alcohol, to form the ester function. FMOC protecting group, in combination with DVB resin derivatized with methoxyalkoxybenzyl alcohol or equivalent linker, can be used for this purpose, with cleavage from the support being effected by TFA in dicholoromethane. Esterification of the suitably activated carboxyl function e.g. with DCC, can then proceed by addition of the desired alcohol, followed by deprotection and isolation of the esterified peptide product.

Incorporation of N-terminal blocking groups can be achieved while the synthesized peptide is still attached to the resin, for instance by treatment with a suitable anhydride and nitrile. To incorporate an acetyl blocking group at the N-terminus, for instance, the resin-coupled peptide can be treated with 20% acetic anhydride in acetonitrile. The N-blocked peptide product can then be cleaved from the resin, deprotected and subsequently isolated.

To ensure that the peptide obtained from either chemical or biological synthetic techniques is the desired peptide, analysis of the peptide composition should be conducted. Such amino acid composition analysis may be conducted using high resolution mass spectrometry to determine the molecular weight of the peptide. Alternatively, or additionally, the amino acid content of the peptide can be confirmed by hydrolyzing the peptide in aqueous acid, and separating, identifying and quantifying the components of the mixture using HPLC, or an amino acid analyzer. Protein sequenators, which sequentially degrade the peptide and identify the amino acids in order, may also be used to determine definitely the sequence of the peptide.

Prior to its use, the peptide may be purified to remove contaminants. In this regard, it will be appreciated that the peptide will be purified so as to meet the standards set out by the appropriate regulatory agencies. Any one of a number of a conventional purification procedures may be used to attain the required level of purity including, for example, reversed-phase high performance liquid chromatography (HPLC) using an alkylated silica column such as $C_4$-, $C_8$- or $C_{18}$-silica. A gradient mobile phase of increasing organic content is generally used to achieve purification, for example, acetonitrile in an aqueous buffer, usually containing a small amount of trifluoroacetic acid. Ion-exchange chromatography can be also used to separate peptides based on their charge.

Substantially pure protein obtained as described herein may be purified by following known procedures for protein purification, wherein an immunological, enzymatic or other assay is used to monitor purification at each stage in the procedure. Protein purification methods are well known in the art, and are described, for example in Deutscher et al. (ed., 1990, *Guide to Protein Purification*, Harcourt Brace Jovanovich, San Diego).

As discussed, modifications or optimizations of peptide ligands of the disclosure are within the scope of the application. Modified or optimized peptides are included within the definition of peptide binding ligand. Specifically, a peptide sequence identified can be modified to optimize its potency, pharmacokinetic behavior, stability and/or other biological, physical and chemical properties.

Amino Acid Substitutions

In certain embodiments, the disclosed methods and compositions may involve preparing peptides with one or more substituted amino acid residues.

In various embodiments, the structural, physical and/or therapeutic characteristics of peptide sequences may be optimized by replacing one or more amino acid residues.

Other modifications can also be incorporated without adversely affecting the activity and these include, but are not limited to, substitution of one or more of the amino acids in the natural L-isomeric form with amino acids in the D-isomeric form. Thus, the peptide may include one or more D-amino acid resides, or may comprise amino acids which are all in the D-form. Retro-inverso forms of peptides in accordance with the present disclosure are also contemplated, for example, inverted peptides in which all amino acids are substituted with D-amino acid forms.

The skilled artisan will be aware that, in general, amino acid substitutions in a peptide typically involve the replacement of an amino acid with another amino acid of relatively similar properties (i.e., conservative amino acid substitutions). The properties of the various amino acids and effect of amino acid substitution on protein structure and function has been the subject of extensive study and knowledge in the art.

For example, one can make the following isosteric and/or conservative amino acid changes in the parent polypeptide sequence with the expectation that the resulting polypeptides would have a similar or improved profile of the properties described above:

Substitution of alkyl-substituted hydrophobic amino acids: including alanine, leucine, isoleucine, valine, norleucine, S-2-aminobutyric acid, S-cyclohexylalanine or other simple alpha-amino acids substituted by an aliphatic side chain from C1-10 carbons including branched, cyclic and straight chain alkyl, alkenyl or alkynyl substitutions.

Substitution of aromatic-substituted hydrophobic amino acids: including phenylalanine, tryptophan, tyrosine, biphenylalanine, 1-naphthylalanine, 2-naphthylalanine, 2-benzothienylalanine, 3-benzothienylalanine, histidine, amino, alkylamino, dialkylamino, aza, halogenated (fluoro, chloro, bromo, or iodo) or alkoxy-substituted forms of the previous listed aromatic amino acids, illustrative examples of which are: 2-,3- or 4-aminophenylalanine, 2-,3- or 4-chlorophenylalanine, 2-,3- or 4-methylphenylalanine, 2-,3- or 4-methoxyphenylalanine, 5-amino-, 5-chloro-, 5-methyl- or 5-methoxytryptophan, 2'-, 3'-, or 4'-amino-, 2'-, 3'-, or 4'-chloro-, 2,3, or 4-biphenylalanine, 2',-3',- or 4'-methyl-2, 3 or 4-biphenylalanine, and 2- or 3-pyridylalanine.

Substitution of amino acids containing basic functions: including arginine, lysine, histidine, ornithine, 2,3-diaminopropionic acid, homoarginine, alkyl, alkenyl, or aryl-substituted (from $C_1$-$C_{10}$ branched, linear, or cyclic) derivatives of the previous amino acids, whether the substituent is on the heteroatoms (such as the alpha nitrogen, or the distal nitrogen or nitrogens, or on the alpha carbon, in the pro-R position for example. Compounds that serve as illustrative examples include: N-epsilon-isopropyl-lysine, 3-(4-tetrahydropyridyl)-glycine, 3-(4-tetrahydropyridyl)-alanine, N,N-gamma, gamma'-diethyl-homoarginine. Included also are compounds such as alpha methyl arginine, alpha methyl 2,3-diaminopropionic acid, alpha methyl histidine, alpha methyl ornithine where alkyl group occupies the pro-R position of the alpha carbon. Also included are the amides formed from alkyl, aromatic, heteroaromatic (where the heteroaromatic group has one or more nitrogens, oxygens, or sulfur atoms singly or in combination) carboxylic acids or any of the many well-known activated derivatives such as acid chlorides, active esters, active azolides and related derivatives) and lysine, ornithine, or 2,3-diaminopropionic acid.

Substitution of acidic amino acids: including aspartic acid, glutamic acid, homoglutamic acid, tyrosine, alkyl, aryl, arylalkyl, and heteroaryl sulfonamides of 2,4-diaminopriopionic acid, ornithine or lysine and tetrazole-substituted alkyl amino acids.

Substitution of side chain amide residues: including asparagine, glutamine, and alkyl or aromatic substituted derivatives of asparagine or glutamine.

Substitution of hydroxyl containing amino acids: including serine, threonine, homoserine, 2,3-diaminopropionic acid, and alkyl or aromatic substituted derivatives of serine or threonine. It is also understood that the amino acids within each of the categories listed above can be substituted for another of the same group.

For example, the hydropathic index of amino acids may be considered (Kyte & Doolittle, 1982, J. Mol. Biol., 157: 105-132). The relative hydropathic character of the amino acid contributes to the secondary structure of the resultant protein, which in turn defines the interaction of the protein with other molecules. Each amino acid has been assigned a hydropathic index on the basis of its hydrophobicity and charge characteristics (Kyte & Doolittle, 1982), these are: isoleucine (+4.5); valine (+4.2); leucine (+3.8); phenylalanine (+2.8); cysteine/cystine (+2.5); methionine (+1.9); alanine (+1.8); glycine (−0.4); threonine (−0.7); serine (−0.8); tryptophan (−0.9); tyrosine (−1.3); proline (−1.6); histidine (−3.2); glutamate (−3.5); glutamine (−3.5); aspartate (−3.5); asparagine (−3.5); lysine (−3.9); and arginine (−4.5). In making conservative substitutions, the use of amino acids whose hydropathic indices are within +/−2 is preferred, within +/−1 are more preferred, and within +/−0.5 are even more preferred.

Amino acid substitution may also take into account the hydrophilicity of the amino acid residue (e.g., U.S. Pat. No. 4,554,101). Hydrophilicity values have been assigned to amino acid residues: arginine (+3.0); lysine (+3.0); aspartate (+3.0); glutamate (+3.0); serine (+0.3); asparagine (+0.2); glutamine (+0.2); glycine (0); threonine (−0.4); proline (−0.5.+−0.1); alanine (−0.5); histidine (−0.5); cysteine (−1.0); methionine (−1.3); valine (−1.5); leucine (−1.8); isoleucine (−1.8); tyrosine (−2.3); phenylalanine (−2.5); tryptophan (−3.4). Replacement of amino acids with others of similar hydrophilicity is preferred.

Other considerations include the size of the amino acid side chain. For example, it would generally not be preferred to replace an amino acid with a compact side chain, such as glycine or serine, with an amino acid with a bulky side chain, e.g., tryptophan or tyrosine. The effect of various amino acid residues on protein secondary structure is also a consideration. Through empirical study, the effect of different amino acid residues on the tendency of protein domains to adopt an alpha-helical, beta-sheet or reverse turn secondary structure has been determined and is known in the art (see, e.g., Chou & Fasman, 1974, Biochemistry, 13:222-245; 1978, Ann. Rev. Biochem., 47:251-276; 1979, Biophys. J., 26:367-384).

Based on such considerations and extensive empirical study, tables of conservative amino acid substitutions have been constructed and are known in the art. For example: arginine and lysine; glutamate and aspartate; serine and threonine; glutamine and asparagine; and valine, leucine and isoleucine. Alternatively: Ala (A) leu, ile, val; Arg (R) gln, asn, lys; Asn (N) his, asp, lys, arg, gln; Asp (D) asn, glu; Cys (C) ala, ser; Gln (Q) glu, asn; Glu (E) gln, asp; Gly (G) ala; His (H) asn, gln, lys, arg; Ile (I) val, met, ala, phe, leu; Leu (L) val, met, ala, phe, ile; Lys (K) gln, asn, arg; Met (M) phe, ile, leu; Phe (F) leu, val, ile, ala, tyr; Pro (P) ala; Ser(S), thr; Thr (T) ser; Trp (W) phe, tyr; Tyr (Y) trp, phe, thr, ser; Val (V) ile, leu, met, phe, ala.

Other considerations for amino acid substitutions include whether or not the residue is located in the interior of a protein or is solvent exposed. For interior residues, conservative substitutions would include: Asp and Asn; Ser and Thr; Ser and Ala; Thr and Ala; Ala and Gly; Ile and Val; Val and Leu; Leu and Ile; Leu and Met; Phe and Tyr; Tyr and Trp. (See, e.g., PROWL Rockefeller University website). For solvent exposed residues, conservative substitutions would include: Asp and Asn; Asp and Glu; Glu and Gln; Glu and Ala; Gly and Asn; Ala and Pro; Ala and Gly; Ala and Ser; Ala and Lys; Ser and Thr; Lys and Arg; Val and Leu; Leu and Ile; Ile and Val; Phe and Tyr. Various matrices have been constructed to assist in selection of amino acid substitutions, such as the PAM250 scoring matrix, Dayhoff matrix, Grantham matrix, McLachlan matrix, Doolittle matrix, Henikoff matrix, Miyata matrix, Fitch matrix, Jones matrix, Rao matrix, Levin matrix and Risler matrix (Idem.)

In determining amino acid substitutions, one may also consider the existence of intermolecular or intramolecular bonds, such as formation of ionic bonds (salt bridges) between positively charged residues (e.g., His, Arg, Lys) and negatively charged residues (e.g., Asp, Glu) or disulfide bonds between nearby cysteine residues.

Methods of substituting any amino acid for any other amino acid in an encoded peptide sequence are well known and a matter of routine experimentation for the skilled artisan, for example by the technique of site-directed mutagenesis or by synthesis and assembly of oligonucleotides encoding an amino acid substitution and splicing into an expression vector construct.

Pharmaceutical Compositions and Administration

The disclosure is also directed to methods of administering the compounds of the disclosure to a subject.

Pharmaceutical compositions comprising the present compounds are administered to a subject in need thereof by any number of routes including, but not limited to, topical, oral, intravenous, intramuscular, intra-arterial, intramedullary, intrathecal, intraventricular, transdermal, subcutaneous, intraperitoneal, intranasal, enteral, topical, sublingual, or rectal means.

In accordance with one embodiment, a method of treating a subject in need of such treatment is provided. The method comprises administering a pharmaceutical composition comprising at least one compound of the present disclosure to a subject in need thereof. Compounds identified by the methods of the disclosure can be administered with known compounds or other medications as well.

The pharmaceutical compositions useful for practicing the disclosure may be administered to deliver a dose of between 1 ng/kg/day and 100 mg/kg/day.

The disclosure encompasses the preparation and use of pharmaceutical compositions comprising a compound useful for treatment of the diseases disclosed herein as an active ingredient. Such a pharmaceutical composition may consist of the active ingredient alone, in a form suitable for administration to a subject, or the pharmaceutical composition may comprise the active ingredient and one or more pharmaceutically acceptable carriers, one or more additional ingredients, or some combination of these. The active ingredient may be present in the pharmaceutical composition in the form of a physiologically acceptable ester or salt, such as in combination with a physiologically acceptable cation or anion, as is well known in the art.

As used herein, the term "physiologically acceptable" ester or salt means an ester or salt form of the active ingredient which is compatible with any other ingredients of the pharmaceutical composition, which is not deleterious to the subject to which the composition is to be administered.

The formulations of the pharmaceutical compositions described herein may be prepared by any method known or hereafter developed in the art of pharmacology. In general, such preparatory methods include the step of bringing the active ingredient into association with a carrier or one or more other accessory ingredients, and then, if necessary or desirable, shaping or packaging the product into a desired single- or multi-dose unit.

It will be understood by the skilled artisan that such pharmaceutical compositions are generally suitable for administration to animals of all sorts. Subjects to which administration of the pharmaceutical compositions of the disclosure is contemplated include, but are not limited to, humans and other primates, mammals including commercially relevant mammals such as cattle, pigs, horses, sheep, cats, and dogs, birds including commercially relevant birds such as chickens, ducks, geese, and turkeys. The disclosure is also contemplated for use in contraception for nuisance animals such as rodents.

A pharmaceutical composition of the disclosure may be prepared, packaged, or sold in bulk, as a single unit dose, or as a plurality of single unit doses. As used herein, a "unit dose" is discrete amount of the pharmaceutical composition comprising a predetermined amount of the active ingredient. The amount of the active ingredient is generally equal to the dosage of the active ingredient which would be administered to a subject or a convenient fraction of such a dosage such as, for example, one-half or one-third of such a dosage.

The relative amounts of the active ingredient, the pharmaceutically acceptable carrier, and any additional ingredients in a pharmaceutical composition of the disclosure will vary, depending upon the identity, size, and condition of the subject treated and further depending upon the route by which the composition is to be administered. By way of example, the composition may comprise between 0.1% and 100% (w/w) active ingredient.

In addition to the active ingredient, a pharmaceutical composition of the disclosure may further comprise one or more additional pharmaceutically active agents. Particularly contemplated additional agents include anti-emetics and scavengers such as cyanide and cyanate scavengers.

Controlled- or sustained-release formulations of a pharmaceutical composition of the disclosure may be made using conventional technology.

As used herein, "additional ingredients" include, but are not limited to, one or more of the following: excipients; surface active agents; dispersing agents; inert diluents; granulating and disintegrating agents; binding agents; lubricating agents; sweetening agents; flavoring agents; coloring agents; preservatives; physiologically degradable compositions such as gelatin; aqueous vehicles and solvents; oily vehicles and solvents; suspending agents; dispersing or wetting agents; emulsifying agents, demulcents; buffers; salts; thickening agents; fillers; emulsifying agents; antioxidants; antibiotics; antifungal agents; stabilizing agents; and pharmaceutically acceptable polymeric or hydrophobic materials. Other "additional ingredients" which may be included in the pharmaceutical compositions of the disclosure are known in the art and described, for example in Genaro, ed., 1985, *Remington's Pharmaceutical Sciences*, Mack Publishing Co., Easton, PA, which is incorporated herein by reference.

Typically, dosages of the compound of the disclosure which may be administered to an animal, preferably a human, range in amount from 1 μg to about 100 g per kilogram of body weight of the animal. While the precise dosage administered will vary depending upon any number of factors, including but not limited to, the type of animal and type of disease state being treated, the age of the animal and the route of administration. In one aspect, the dosage of the compound will vary from about 1 mg to about 10 g per kilogram of body weight of the animal. In another aspect, the dosage will vary from about 10 mg to about 1 g per kilogram of body weight of the animal.

The compound may be administered to an animal as frequently as several times daily, or it may be administered less frequently, such as once a day, once a week, once every two weeks, once a month, or even less frequently, such as once every several months or even once a year or less. The frequency of the dose will be readily apparent to the skilled artisan and will depend upon any number of factors, such as, but not limited to, the type of cancer being diagnosed, the type and severity of the condition or disease being treated, the type and age of the animal, etc.

Suitable preparations include injectables, either as liquid solutions or suspensions, however, solid forms suitable for solution in, suspension in, liquid prior to injection, may also be prepared. The preparation may also be emulsified, or the polypeptides encapsulated in liposomes. The active ingredients are often mixed with excipients which are pharmaceutically acceptable and compatible with the active ingredient. Suitable excipients are, for example, water saline, dextrose, glycerol, ethanol, or the like and combinations thereof. In addition, if desired, the vaccine preparation may also include minor amounts of auxiliary substances such as wetting or emulsifying agents, pH buffering agents, and/or adjuvants.

The disclosure also includes a kit comprising the composition of the disclosure and an instructional material which describes adventitially administering the composition to a cell or a tissue of a subject. In another embodiment, this kit comprises a (preferably sterile) solvent suitable for dissolving or suspending the composition of the disclosure prior to administering the compound to the subject.

As used herein, an "instructional material" includes a publication, a recording, a diagram, or any other medium of expression which can be used to communicate the usefulness of the peptide of the disclosure in the kit for effecting alleviation of the various diseases or disorders recited herein. Optionally, or alternately, the instructional material may describe one or more methods of using the compositions for diagnostic or identification purposes or of alleviation the diseases or disorders in a cell or a tissue of a mammal. The instructional material of the kit of the disclosure may, for example, be affixed to a container which contains the multimeric peptide of the disclosure or be shipped together with a container which contains the peptide. Alternatively, the instructional material may be shipped separately from the container with the intention that the instructional material and the compound be used cooperatively by the recipient.

Linkers

In one embodiment, linkers are used to link each peptide of the multimer peptide constructs of the disclosure.

Additionally, modifications encompassed by the disclosure include introduction of linkers or spacers between the targeting sequence of the binding moiety or binding polypeptide and the detectable label or therapeutic agent. For example, use of such linkers/spacers can improve the relevant properties of the binding peptides (e.g., increase serum stability, etc.). These linkers can include, but are not restricted to, substituted or unsubstituted alkyl chains, polyethylene glycol derivatives, amino acid spacers, sugars, or aliphatic or aromatic spacers common in the art.

For example, suitable linkers include homobifunctional and heterobifunctional cross-linking molecules. The homobifunctional molecules have at least two reactive functional groups, which are the same. The reactive functional groups on a homobifunctional molecule include, for example, aldehyde groups and active ester groups. Homobifunctional molecules having aldehyde groups include, for example, glutaraldehyde and subaraldehyde.

Homobifunctional linker molecules having at least two active ester units include esters of dicarboxylic acids and N-hydroxysuccinimide. Some examples of such N-succinimidyl esters include disuccinimidyl suberate and dithio-bis-(succinimidyl propionate), and their soluble bis-sulfonic acid and bis-sulfonate salts such as their sodium and potassium salts.

Heterobifunctional linker molecules have at least two different reactive groups. Some examples of heterobifunctional reagents containing reactive disulfide bonds include N-succinimidyl 3-(2-pyridyl-dithio) propionate (Carlsson et al., 1978. Biochem. J., 173:723-737), sodium S-4-succinimidyloxycarbonyl-alpha-methylbenzylthiosulfate, and 4-succinimidyloxycarbonyl-alpha-methyl-(2-pyridyldithio) toluene. N-succinimidyl 3-(2-pyridyldithio) propionate is preferred. Some examples of heterobifunctional reagents comprising reactive groups having a double bond that reacts with a thiol group include succinimidyl 4-(N-maleimidomethyl) cyclohexahe-1-carboxylate and succinimidyl m-maleimidobenzoate. Other heterobifunctional molecules include succinimidyl 3-(maleimido) propionate, sulfosuccinimidyl 4-(p-maleimido-phenyl) butyrate, sulfosuccinimidyl 4-(N-maleimidomethyl-cyclohexane)-1-carboxylate, maleimidobenzoyl-5N-hydroxy-succinimide ester.

Furthermore, linkers that are combinations of the molecules and/or moieties described above, can also be employed to confer special advantage to the properties of the peptide. Lipid molecules with linkers may be attached to allow formulation of ultrasound bubbles, liposomes or other aggregation based constructs. Such constructs could be employed as agents for targeting and delivery of a diagnostic reporter, a therapeutic agent (e.g., a chemical "warhead" for therapy), or a combination of these.

Constructs employing dimers, multimers, or polymers of one or more peptide ligands of the disclosure are also contemplated. Indeed, there is ample literature evidence that the binding of low potency peptides or small molecules can be substantially increased by the formation of dimers and multimers. Thus, dimeric and multimeric constructs (both homogeneous and heterogeneous) are within the scope of the instant disclosure. The polypeptide sequences in the dimeric constructs can be attached at their N- or C-terminus or the N-epsilon nitrogen of a suitably placed lysine moiety (or another function bearing a selectively derivatizable group such as a pendant oxyamino or other nucleophilic group), or can be joined together via one or more linkers (e.g., those discussed herein) employing the appropriate attachment chemistry. This coupling chemistry can include amide, urea, thiourea, oxime, or aminoacetylamide (from chloro- or bromoacetamide derivatives, but is not so limited). For example, methods to prepare dimeric or multimeric constructs of Plec1 binding polypeptides of the disclosure include at least those discussed below.

Linkers can also be used for attachment to a chelating agent.

Therapeutic Agents

In other embodiments, therapeutic agents, including, but not limited to, cytotoxic agents, anti-angiogenic agents, pro-apoptotic agents, antibiotics, hormones, hormone antagonists, chemokines, drugs, prodrugs, toxins, enzymes or other agents may be used as adjunct therapies when using the multimeric peptide ligand complexes described herein. Drugs useful in the disclosure may, for example, possess a pharmaceutical property selected from the group consisting of antimitotic, antikinase, alkylating, antimetabolite, antibiotic, alkaloid, anti-angiogenic, pro-apoptotic agents, and combinations thereof.

Techniques for detecting and measuring these agents are provided in the art or described herein.

Aptamers

The present disclosure is also directed to useful aptamers. In one embodiment, an aptamer is a compound that is selected in vitro to bind preferentially to another compound (in this case the identified proteins). In one aspect, aptamers are nucleic acids or peptides, because random sequences can be readily generated from nucleotides or amino acids (both naturally occurring and synthetically made) in large numbers but of course they need not be limited to these. In another aspect, the nucleic acid aptamers are short strands of DNA that bind protein targets. In one aspect, the aptamers are oligonucleotide aptamers. Oligonucleotide aptamers are oligonucleotides which can bind to a specific protein sequence of interest. A general method of identifying aptamers is to start with partially degenerate oligonucleotides, and then simultaneously screen the many thousands of oligonucleotides for the ability to bind to a desired protein. The bound oligonucleotide can be eluted from the protein and sequenced to identify the specific recognition sequence. Transfer of large amounts of a chemically stabilized aptamer into cells can result in specific binding to a polypeptide of interest, thereby blocking its function. [For example, see the following publications describing in vitro selection of aptamers: Klug et al., Mol. Biol. Reports 20:97-107 (1994); Wallis et al., Chem. Biol. 2:543-552 (1995); Ellington, Curr. Biol. 4:427-429 (1994); Lato et al., Chem. Biol. 2:291-303 (1995); Conrad et al., Mol. Div. 1:69-78 (1995); and Uphoff et al., Curr. Opin. Struct. Biol. 6:281-287 (1996)].

Aptamers offer advantages over other oligonucleotide-based approaches that artificially interfere with target gene function due to their ability to bind protein products of these genes with high affinity and specificity. However, RNA aptamers can be limited in their ability to target intracellular proteins since even nuclease-resistant aptamers do not efficiently enter the intracellular compartments. Moreover, attempts at expressing RNA aptamers within mammalian cells through vector-based approaches have been hampered by the presence of additional flanking sequences in expressed RNA aptamers, which may alter their functional conformation.

The idea of using single-stranded nucleic acids (DNA and RNA aptamers) to target protein molecules is based on the ability of short sequences (20 mers to 80 mers) to fold into unique 3D conformations that enable them to bind targeted proteins with high affinity and specificity. RNA aptamers have been expressed successfully inside eukaryotic cells, such as yeast and multicellular organisms, and have been shown to have inhibitory effects on their targeted proteins in the cellular environment.

In binding assays, the interaction is binding and the complex formed can be isolated or detected in the reaction mixture. In a particular embodiment, one of the peptides of the complexes described herein, or the test compound or drug candidate is immobilized on a solid phase, e.g., on a microtiter plate, by covalent or non-covalent attachments. Non-covalent attachment generally is accomplished by coating the solid surface with a solution of the peptide and drying. Alternatively, an immobilized antibody, e.g., a monoclonal antibody, specific for the peptide to be immobilized can be used to anchor it to a solid surface. The assay is performed by adding the non-immobilized component, which may be labeled by a detectable label, to the immobilized component, e.g., the coated surface containing the anchored component. When the reaction is complete, the non-reacted components are removed, e.g., by washing, and complexes anchored on the solid surface are detected. When the originally non-immobilized component carries a detectable label, the detection of label immobilized on the surface indicates that complexing occurred. Where the originally non-immobilized component does not carry a label, complexing can be detected, for example, by using a labeled antibody specifically binding the immobilized complex.

The present disclosure also encompasses pharmaceutical and therapeutic compositions comprising the multimeric peptide ligand complexes of the present disclosure. More particularly, such compounds can be formulated as pharmaceutical compositions using standard pharmaceutically acceptable carriers, fillers, solubilizing agents and stabilizers known to those skilled in the art.

The present disclosure further provides a pharmaceutical preparation comprising one or more of the multimeric peptide ligands or complexes of the disclosure. The concentration of the polypeptide in the pharmaceutical composition can vary widely, i.e., from less than about 0.1% by weight, usually being at least about 1% by weight to as much as 20% by weight or more.

The composition may comprise a pharmaceutically acceptable carrier in addition to the active ingredient. The pharmaceutical carrier can be any compatible, non-toxic substance suitable to deliver the peptides o to the patient. For polypeptides, sterile water, alcohol, fats, waxes, and inert solids may be used as the carrier. Pharmaceutically acceptable adjuvants, buffering agents, dispersing agents, and the like, may also be incorporated into the pharmaceutical compositions.

Methods of producing pharmaceutical compositions comprising polypeptides are described in U.S. Pat. Nos. 5,789,543 and 6,207,718. The preferred form depends on the intended mode of administration and therapeutic application.

In one embodiment, the present compositions comprising multimeric peptides are administered by injection. The parenteral route for administration of the polypeptide is in accordance with known methods, e.g. injection or infusion by intravenous, intraperitoneal, intramuscular, intra-arterial, subcutaneous, or intralesional routes. The protein or polypeptide may be administered continuously by infusion or by bolus injection. A typical composition for intravenous infusion could be made up to contain 10 to 50 ml of sterile 0.9% NaCl or 5% glucose optionally supplemented with a 20% albumin solution and between 10 μg and 50 mg, preferably between 50 μg and 10 mg, of the polypeptide. A typical pharmaceutical composition for intramuscular injection would be made up to contain, for example, 1-10 ml of sterile buffered water and between 10 μg and 50 mg, preferably between 50 μg and 10 mg, of the polypeptide of the present disclosure. Methods for preparing parenterally administrable compositions are well known in the art and described in more detail in various sources, including, for example, Remington's Pharmaceutical Science (15th ed., Mack Publishing, Easton, Pa., 1980) (incorporated by reference in its entirety for all purposes).

Other techniques known in the art may be used in the practice of the present disclosure.

Function of LRP1 During Remyelination

Chronic demyelination exposes neurons and makes them more prone to neurodegeneration. This is the major cause of disabilities in MS patients over time. Unfortunately, currently approved therapies are only aimed at dampening the immune response and fail to address the critical need for stimulating myelin repair during and/or after an MS attack. Understanding the mechanisms of remyelination is critical in preventing neuronal loss, and is paramount to improving the quality of life of MS patients.

The adult CNS contains a large population of OPC that have the potential to differentiate into mature oligodendrocytes and remyelinate denuded axons. Although OPC are efficiently recruited into MS lesions, the process of axon remyelination is still impaired. OPC differentiation into mature oligodendrocytes is inhibited by myelin debris, which can linger in the area of MS plaques, where demyelination took place.

Low-density lipoprotein-Related Protein 1 (LRP1) is a member of the LDL receptor gene family that functions in receptor-mediated endocytosis and cell signaling. LRP1 functions as a phagocytic receptor for myelin in many cell types, including OPC. LRP1 expression in neurons contributes to myelin-mediated inhibition of axonal regeneration.

OPC express LRP1. LRP1 in OPC contributes to the myelin-mediated blocking of remyelination. siRNA-mediated inhibition of LRP1 expression in primary OPC allows the cells to overcome myelin inhibition and differentiate in vitro. LRP1 deletion in cultures of primary OPC enables their differentiation into myelinating oligodendrocytes in the presence of myelin debris. Specific deletion of LRP1 in OPC enhances myelination in an animal model of demyelination. Therefore, LRP1 and the signaling cascade activated downstream of LRP1 in OPC are potential new targets for therapy development.

Neuronal LRP1 binds MAG, OMgp and Nogo, protein components of myelin that mediate inhibition of axonal regeneration following injury. MAG binding to LRP1 promotes the formation of a complex with p75NTR, which activates Rho-A small GTPase. Rho-A activation blocks actin polymerization and prevents axonal extension. Rho-A activation in neurons inhibits axonal regeneration. MAG induces a robust activation of Rho-A in a neuronal cell line. Myelin component Lingo-1 is another powerful inhibitor of myelination via activation of Rho-A. Increased Rho-A activity is not detected if LRP1 is silenced, demonstrating that LRP1 is necessary to initiate Rho-A activation downstream of MAG.

Rho-A has also been shown to be necessary for myelin-mediated inhibition of OPC maturation by a similar mechanism. The mechanism of action of p75NTR-LRP1 in neurons can be extrapolated to OPC differentiation in the presence of myelin. First, OPC express LRP1, and it is well established that OPC express p75NTR. Secondly, myelin debris can activate Rho-A in cultures of OPC, and inhibition of Rho-A restores differentiation of OPC into oligodendrocytes. Finally, the myelin receptor Lingo-1, a negative regulator of OPC differentiation, is not able to initiate Rho-A activation when p75NTR is inhibited.

The role of LRP1 during remyelination shows that targeting LRP1 ligands and blocking downstream signaling partners is an approach to promote remyelination. Such techniques can be used to treat and/or alleviate the symptoms of MS, including RRMS.

As described herein, inhibiting LRP1 function, expression, levels, or synthesis can be achieved by administering to a subject in need thereof a LRP1-targeting siRNA (siLRP1). The siRNA can target one or more sequences selected from the group consisting of SEQ ID NOs: 1-8. Administering siLRP1 can be done as understood in the art, for example, as part of a pharmaceutical composition, in a therapeutically effective amount, and/or with one or more additional therapeutic agents. The inhibition of LRP1 function, expression, levels, or synthesis can be accomplished in OPC. The administration of LRP1-targeting siRNA can promote remyelination, which in turn can alleviate the symptoms of MS and/or treat MS.

Similarly, LRP1-targeting siRNA can be used in a method for inhibiting pathological activation of Rho-A. In this method, siLRP1 can be administered to a subject in need thereof. The siRNA can target one or more sequences selected from the group consisting of SEQ ID NOs: 1-8. Administering siLRP1 can be done as understood in the art, for example, as part of a pharmaceutical composition, in a therapeutically effective amount, and/or with one or more additional therapeutic agents. The inhibition of pathological activation of Rho-A can be accomplished in OPC. The administration of LRP1-targeting siRNA can promote remyelination, which in turn can alleviate the symptoms of MS and/or treat MS.

LRP1-targeting siRNA can also be used in methods of treating myelin-mediated inhibition of axonal regeneration. The siRNA can target one or more sequences selected from the group consisting of SEQ ID NOs: 1-8. The LRP1-targeting siRNA can be administered to a subject in need thereof and in a manner as understood in the art, for example, as part of a pharmaceutical composition, in a therapeutically effective amount, and/or with one or more additional therapeutic agents.

LRP1-targeting siRNA can also be used in methods of maintaining or increasing neuronal viability. The siRNA can target one or more sequences selected from the group consisting of SEQ ID NOs: 1-8. The LRP1-targeting siRNA can be administered to a subject in need thereof and in a manner as understood in the art, for example, as part of a pharmaceutical composition, in a therapeutically effective amount, and/or with one or more additional therapeutic agents.

The present disclosure also provides transgenic mice with the deletion of LRP1 specifically in OPC (LRP1$^{fl/fl}$_Olig1-Cre$^{+}$ mice). LR LRP1$^{fl/fl}$-Olig1-Cre$^{+}$ mice are viable and fertile. Furthermore, using the cuprizone model of demyelination and remyelination, LRP1$^{fl/fl}$-Olig1-Cre$^{+}$ mice have accelerated remyelination when compared to control. LRP1$^{fl/fl}$-Olig1-Cre$^{+}$ mice also have a delayed disease onset when compared to controls in experimental autoimmune encephalomyelitis (EAE), a mouse model of MS.

The transgenic mice, i.e., the LRP1$^{fl/fl}$_Olig1-Cre$^{+}$ mice, can be used to provide an OPC cell culture. Specifically, one or more OPC can be cultured from the transgenic mouse. Further, the OPC can be cultured with one or more other cell populations to prepare a co-culture system.

The mice can also be used in methods for screening candidate therapeutic agents for MS in vivo. For example, a candidate therapeutic for treating or diminishing the symptoms of MS can be administered to the transgenic mouse. Remyelination, or alternatively, persistence of demyelination, can be assessed in the mouse. Further, the mouse can be administered a cuprizone diet or subjected to EAE to model MS symptoms, e.g., demyelination.

The present methods and compositions are now described with reference to the following Examples. Without further description, it is believed that one of ordinary skill in the art can, using the preceding description and the following illustrative examples, make and utilize the present disclosure and practice the claimed methods. The following working examples therefore, are provided for the purpose of illustration only and specifically point out the preferred embodiments of the present disclosure, and are not to be construed as limiting in any way the remainder of the disclosure. Therefore, the examples should be construed to encompass any and all variations which become evident as a result of the teaching provided herein.

EXAMPLES

Example 1—Expression of LRP1 in OPC

Cultures of OPC isolated from rats express LRP1, while LRP1 is not detectable in myelin preparations isolated from adult brain. FIG. 1A is an immunoblot for LRP1 expression in OPC and purified myelin. Myelin basic protein (MBP) is used as a myelination marker and tubulin as a loading control. This immunoblot shows that LRP1 is likely not expressed in mature oligodendrocytes.

Figure 1B:
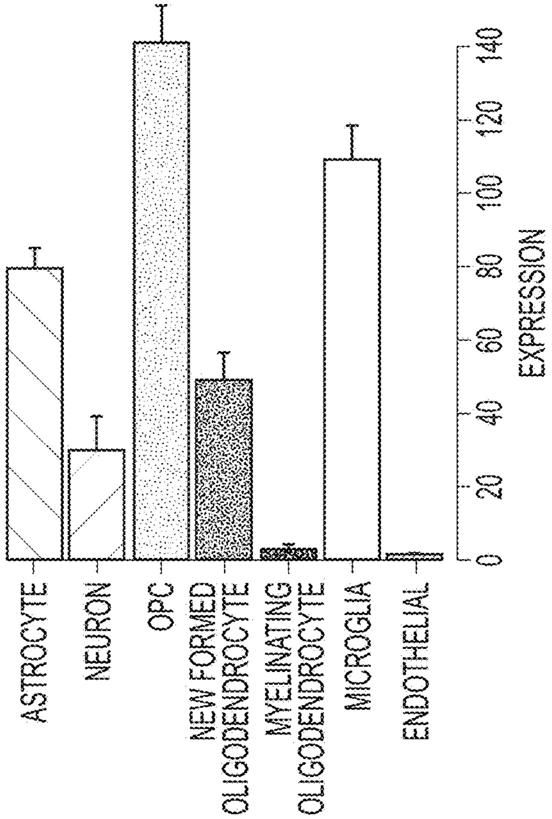
FIG. 1B is a graph showing expression of LRP1 transcript in various stages of OPC differentiation, as determined by gene array.

FIG. 1B shows expression of LRP1 transcript in various stages of OPC differentiation, as determined by gene array. As shown in this figure, OPC express the highest amount of the LRP1 transcript in the CNS, while there is progressive downregulation of LRP1 during their differentiation into myelinating oligodendrocytes.

Figure 1C:
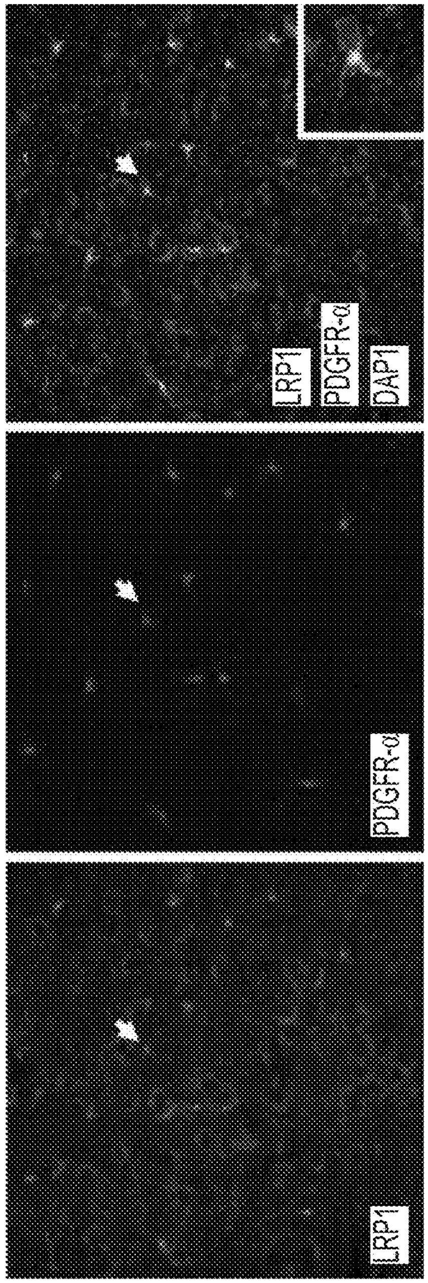
FIG. 1C shows immunofluorescence for LRP1 in an adult mouse brain.

To confirm LRP1 expression in OPC, immunofluorescence is performed on sections of adult mouse brain. Cells characterized as OPC by expression of PDGFR-α are LRP1 positive, as shown in FIG. 1C. In the CNS, LRP1 expression is not limited to OPC. LRP1 expression is also evident in neurons, astrocytes and myeloid cells. These data collectively indicate that LRP1 is preferentially expressed in immature, non-myelinating OPC.

Example 2—Development of an Animal Model for Studying the Function of LRP1 in OPC To study the function of LRP1 in OPC in vivo, LRP1$^{fl/fl}$ mice are crossed with mice expressing the Cre recombinase under the Olig1 promoter. The Olig1 promoter expression is reported selectively in OPC and oligodendrocytes, and is ideally suited to study the function of LRP1 in myelin-mediated inhibition of OPC differentiation. LRP1$^{fl/fl}$ Olig1-Cre$^{+}$ mice are born according to Mendelian ratios, and appear healthy and fertile.

Figure 2A:
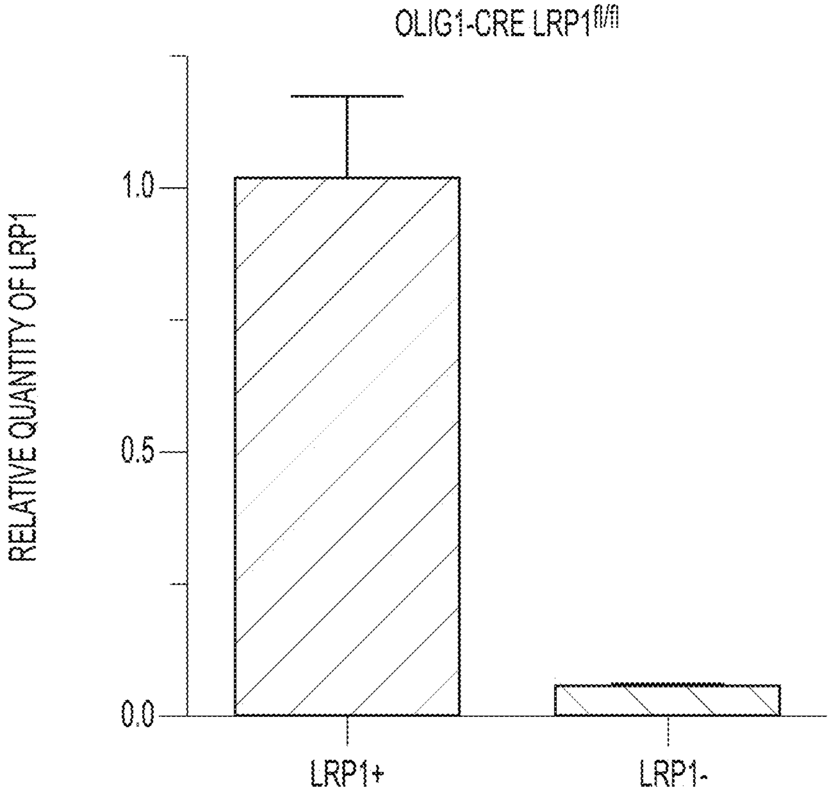
FIGS. 2A and 2B show LRP1 expression by qPCR and immunoblot, respectively, in primary OPC isolated from $LRP1^{fl/fl}$Olig1-Cre+ mice (LRP1−) and $LRP1^{fl/fl}$ Olig1-$Cre^{-}$ mice (LRP1+).
Figure 2B:
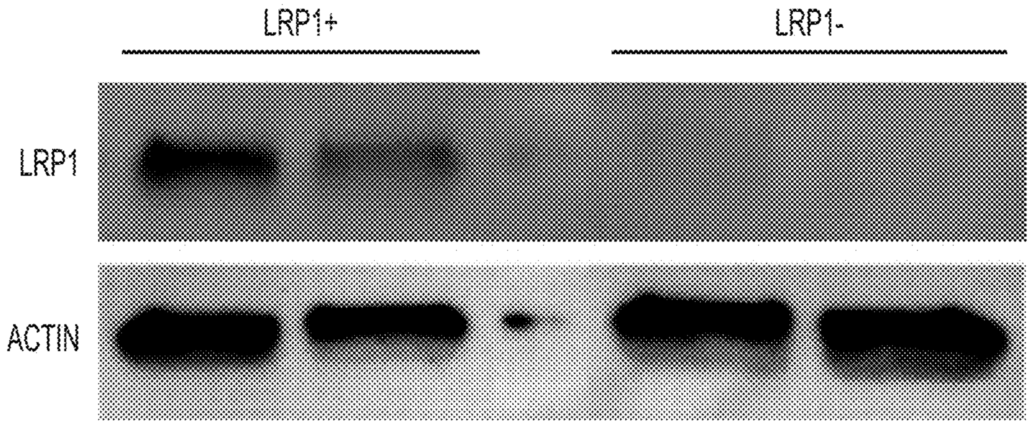

As shown in FIG. 2, OPC from LRP1$^{fl/fl}$Olig1-Cre$^{+}$ (LRP1−) and LRP1$^{fl/fl}$ Olig1-Cre$^{-}$ (LRP1+) mice are isolated from newborn mice by immuno-panning, and immediately analyzed for LRP1 expression by qPCR and immunoblot. As shown in FIG. 2A, LRP1 expression is reduced by ~20-fold in LRP1$^{fl/fl}$Olig1-Cre$^{+}$ OPC, when compared to control OPC. This observation was confirmed by immunoblot analysis (shown in FIG. 2B). LRP1 is undetectable at the protein level in purified OPC isolated from LRP1$^{fl/fl}$Olig1-Cre$^{+}$, when compared to LRP1$^{fl/fl}$Olig1-Cre$^{+}$. This finding confirms deletion of LRP1 in OPC of LRP1$^{fl/fl}$Olig1-Cre$^{+}$ mice.

Figure 3A:
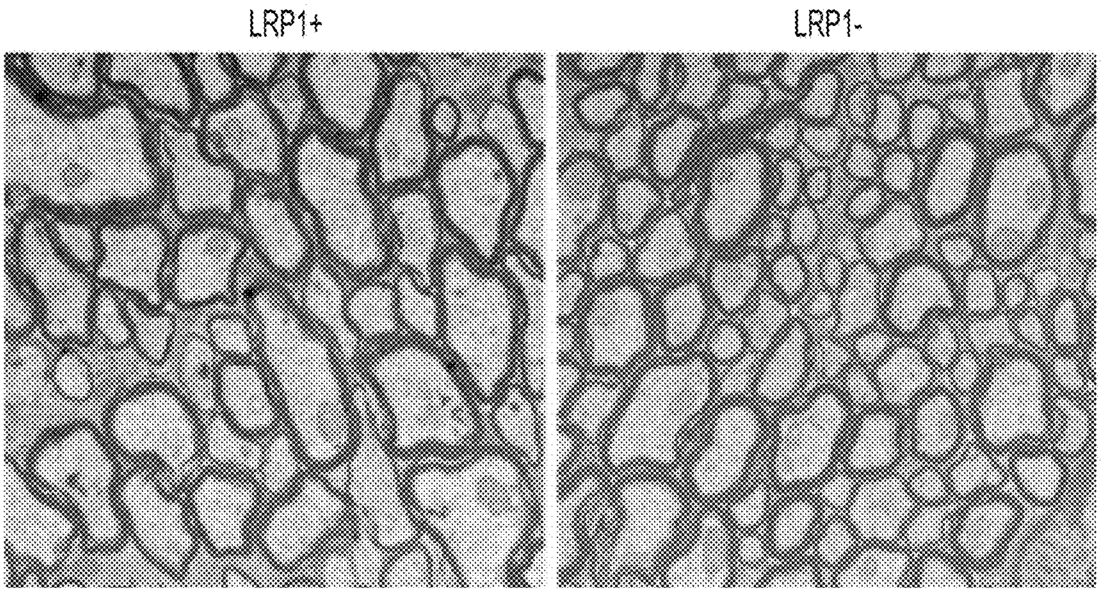
FIGS. 3A and 3B are a transmission electron microscopy (TEM) image and a g-ratio graph, respectively, of myelin structure in the optic nerves of LRP1+ and LRP1− mice.
Figure 3B:
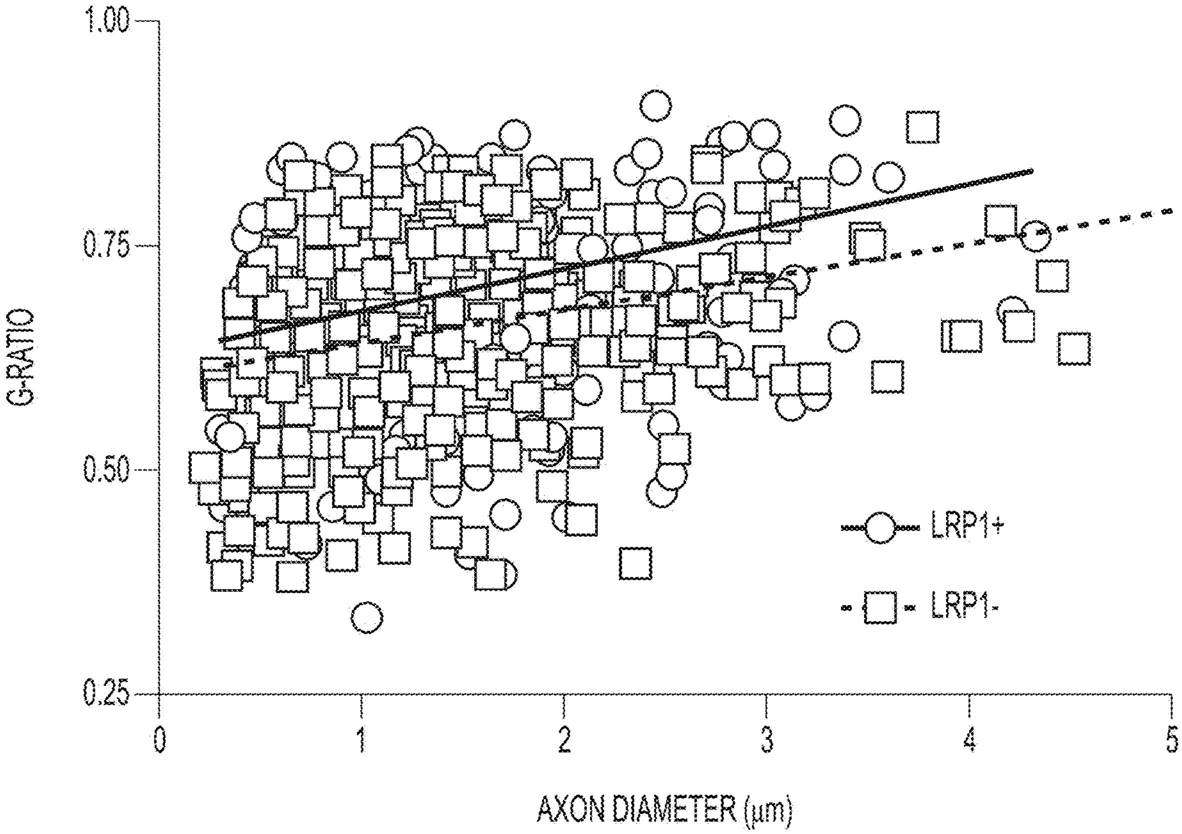

Example 3-Myelin Formation During CNS Development is not Impaired in Animals Lacking LRP1 in OPC To analyze the contribution of LRP1 expression in OPC to myelin ultrastructure, optic nerves from 8-week old $LRP1^{fl/fl}$Olig1-$Cre^+$ and $LRP1^{+/+}$ Olig1-$Cre^+$ mice (4 mice/group) are prepared for transmission electron microscopy (TEM) analysis of the myelin structure and determination of the g-ratio. As shown in FIG. 3A, overall myelin structure in adult mice appears normal following deletion of LRP1 in OPC. Linear fitting of the g-ratio data shows no major differences between the control and experimental groups (FIG. 3B, 10 fields per mouse, with 4 mice/group). This result demonstrates that myelination during development is not impaired in this animal model. The formation of myelin during development is not associated with death of oligodendrocytes and the generation of myelin debris.

Figure 4A:
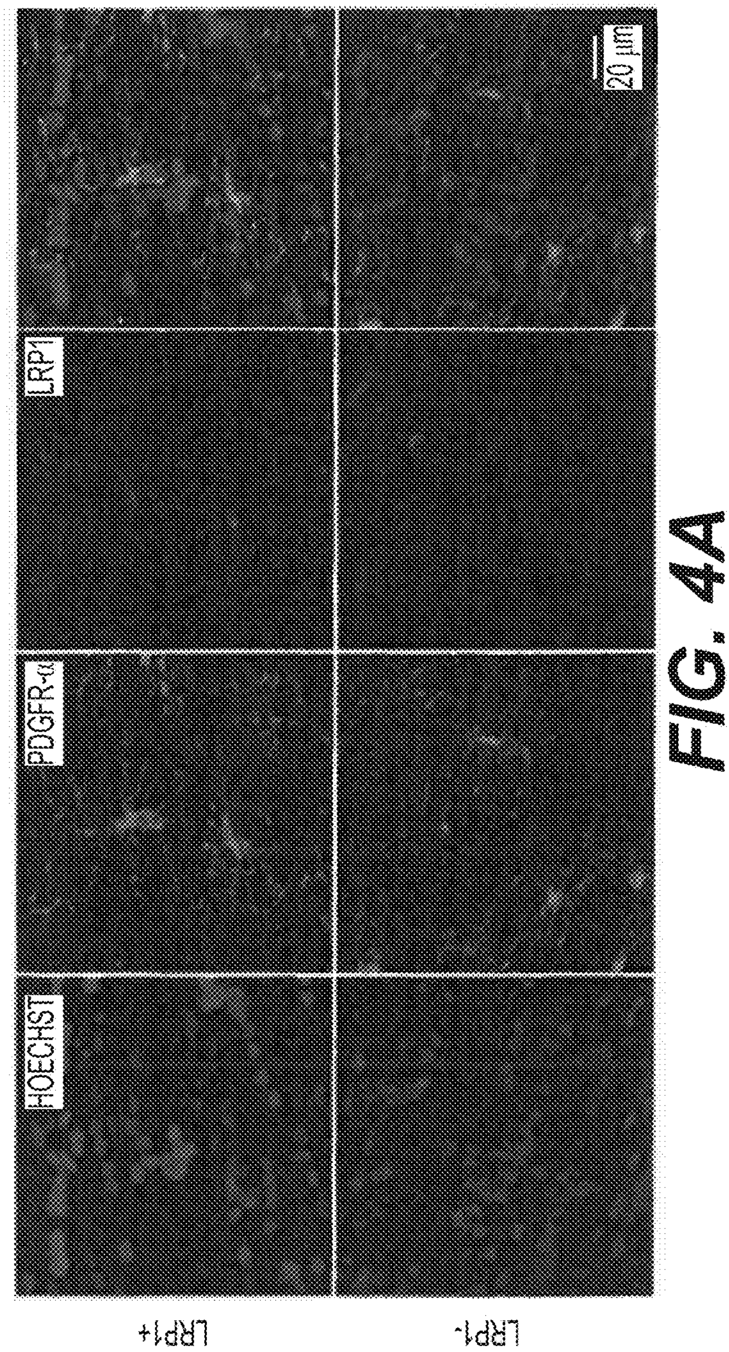
FIG. 4A shows staining for LRP1 and PDGFR-α in LRP1+ and LRP1− mice.
Figure 4B:
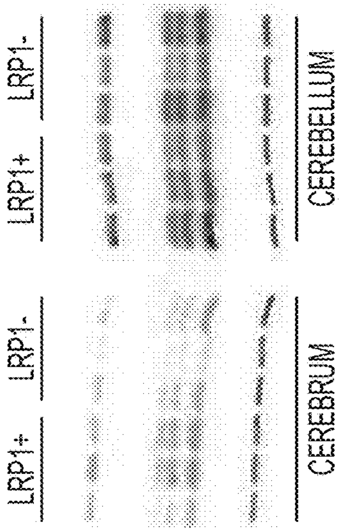
FIGS. 4B and 4C show Western blot and dosimetry analysis, respectively, of CNP and MBP protein in the cerebrum and cerebellum of LRP1+ and LRP1− mice.
Figure 4C:
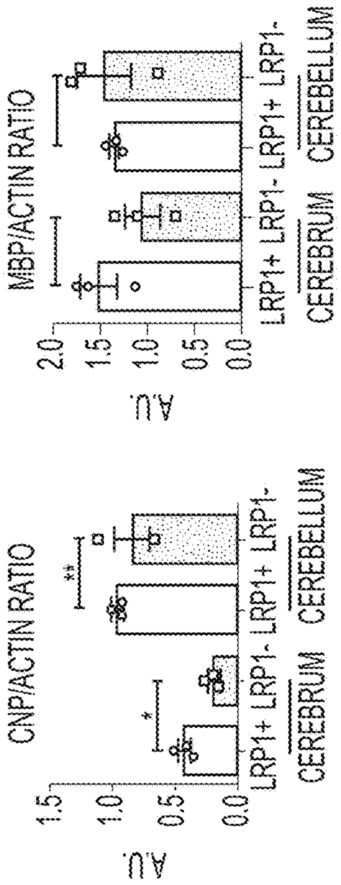

Example 4-LRP1 Deletion in Oligodendroglial Lineage does not Result in Aberrant Myelination Defects LRP1− mice are compared with LRP1+ mice by staining for LRP1 and PDGFRa, as shown in FIG. 4A. The two groups of mice are also compared using Western blot and densitometry analysis of CNP and MBP protein in the cerebrum and cerebellum (*P=0.0207, t-test, n=3 per genotype). This comparison is shown in FIGS. 4B and 4C, respectively.

Example 5-Remyelination is Accelerated in Mice Lacking LRP1 in OPC

To understand the contribution of LRP1 during myelin repair, $LRP1^{fl/fl}$Olig1-$Cre^+$ mice and $LRP1^{+/+}$ Olig1-$Cre^+$ mice are subjected to the cuprizone model of demyelination. Cuprizone is a copper chelator that induces demyelination in the area of corpus callosum (CC) when administered in the mouse diet. Cuprizone inhibits the mitochondrial respiratory chain complex-2 and activates the cellular stress response, ultimately leading to the apoptosis of oligodendrocytes. Once the animals are returned to their regular diet, remyelination takes place in the affected areas.

Figure 5A:
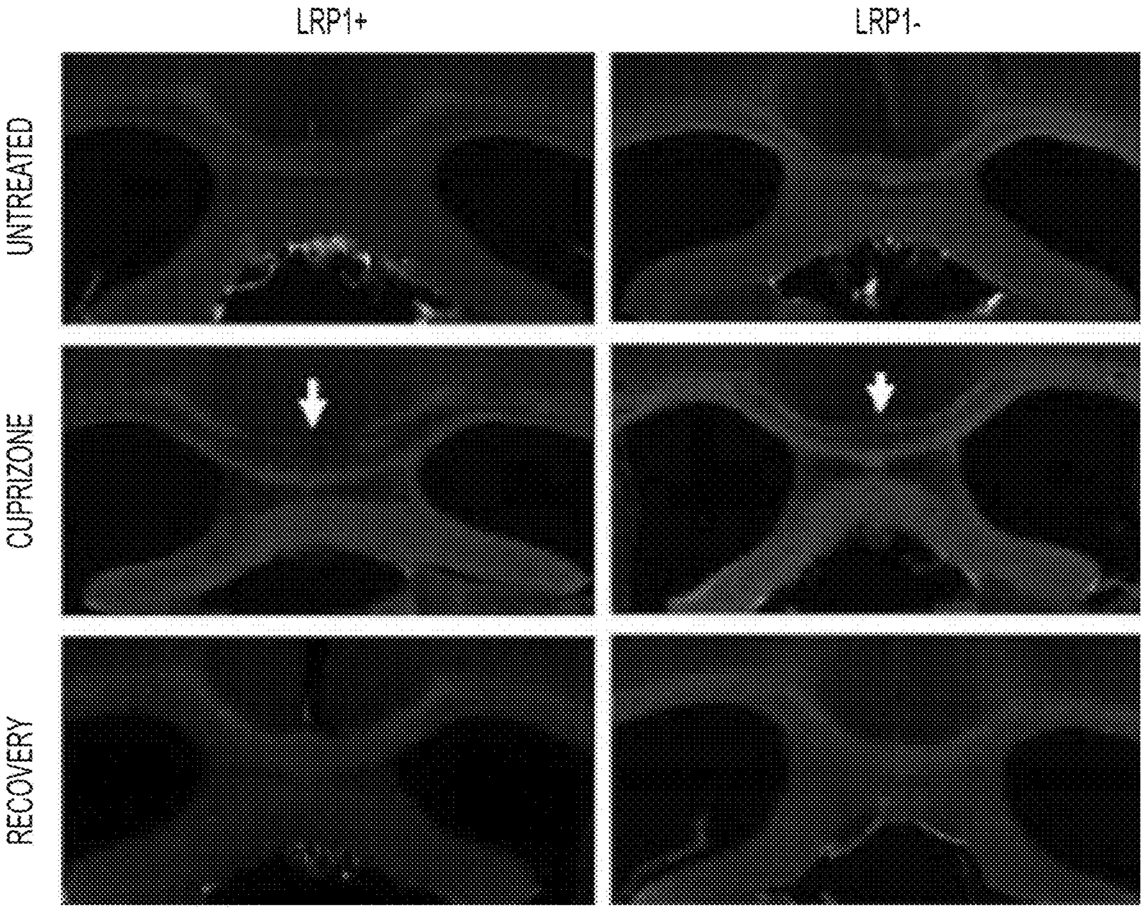
FIGS. 5A and 5B show myelination in the corpus callossum assessed from cuprizone induced demyelination (untreated, five weeks on cuprizone diet, and three weeks after end of cuprizone diet).

$LRP1^{fl/fl}$Olig1-$Cre^+$ mice and $LRP1^{+/+}$ Olig1-$Cre^+$ mice are fed cuprizone (5 weeks at 0.3% w/w) and then return to a normal diet for 3 weeks. Myelination status is determined, either immediately after withdrawal of cuprizone from the diet or three weeks post-recovery, by staining coronal sections of the brain with an antibody against the myelin basic protein (MBP). As shown in FIG. 5A (top panels), baseline myelination prior to administration of cuprizone appears comparable between $LRP1^{+/+}$ Olig1-$Cre^+$ (LRP1+ and $LRP1^{fl/fl}$Olig1-$Cre^+$ (LRP1−) mice, as expected from the electron microscopy results of Example 3 (FIG. 3). However, after 5 weeks on cuprizone, demyelination area (area devoid of MBP immunoreactivity, arrow) is significantly larger in wild type mice than those lacking LRP1 expression in OPC (FIG. 5A, middle panels).

Figure 5B:
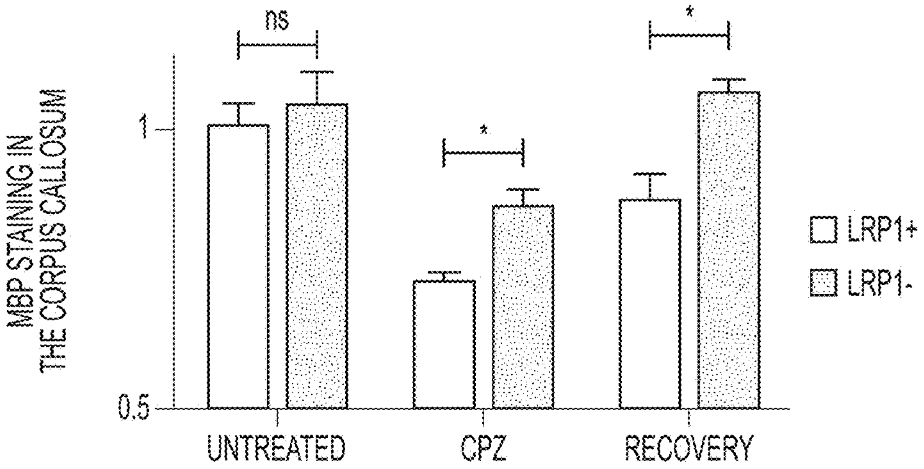

Quantification of the demyelination in the CC is performed confirms that MBP staining is more intense in mice with LRP1 deficiency in OPC, suggesting increased levels of myelination at this stage (FIG. 5B). Further, when mice are examined three weeks after returning to a normal diet, myelination in $LRP1^{fl/fl}$Olig1-$Cre^+$ mice appears comparable to that observed in healthy mice (as assessed by the MBP staining intensity), while in the wild type ($LRP1^{+/+}$ Olig1-$Cre^+$) mice MBP intensity is not as high, indicating incomplete remyelination at this stage (FIG. 5B).

Figure 6A:
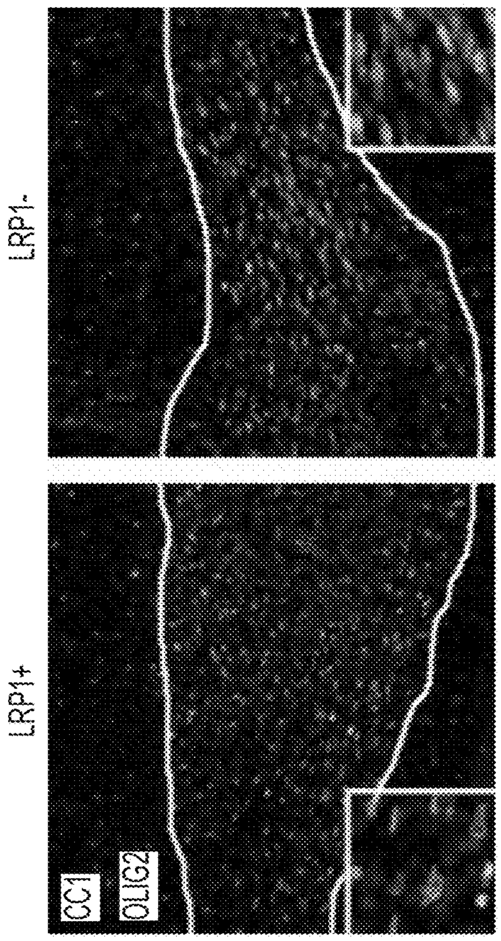
FIGS. 6A and 6B show images and quantification, respectively, of oligodendrocytes, characterized as Olig2/CC1 positive, in the corpus callossum in LRP1+ and LRP1− mice.
Figure 6B:
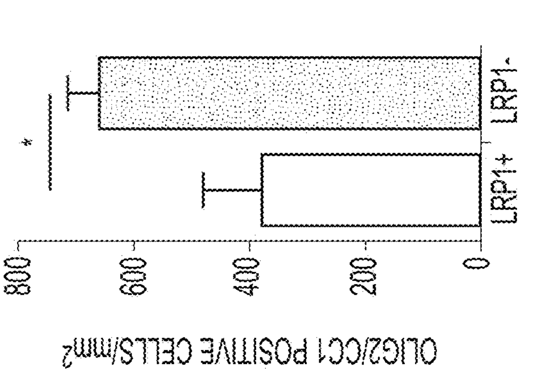

To confirm this observation, sections of the CC are stained for a marker of mature oligodendrocytes after 5 weeks of cuprizone treatment (Olig2/CC1 double positive cells). The results are shown in FIG. 6A (representative pictures) and 6B (quantification of oligodendrocyte in the CC). CC of mice lacking LRP1 expression in OPC present with more oligodendrocytes than the control animals. Collectively, these results indicate that deletion of LRPlin OPC is associated with increased myelination after cuprizone-induced demyelination.

Figure 7A:
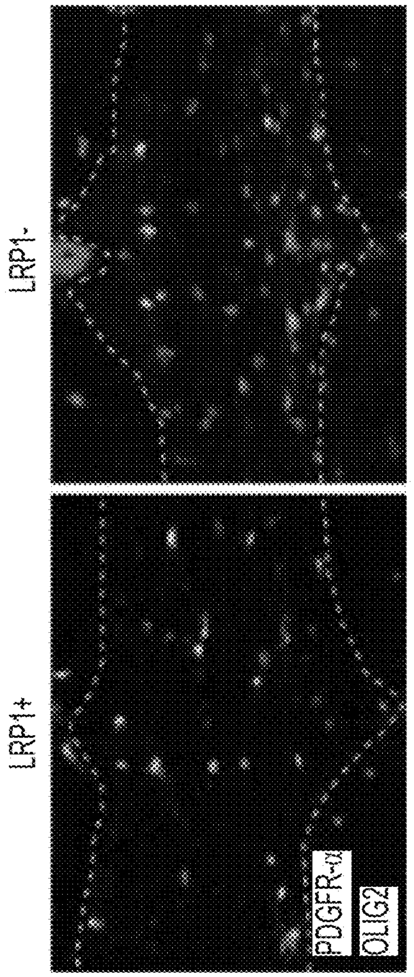
FIGS. 7A and 7B show images and quantification, respectively, of oligodendrocytes, characterized as expressing Olig2 and PDGFR-α, in the corpus callossum in LRP1+ and LRP1− mice.
Figure 7B:
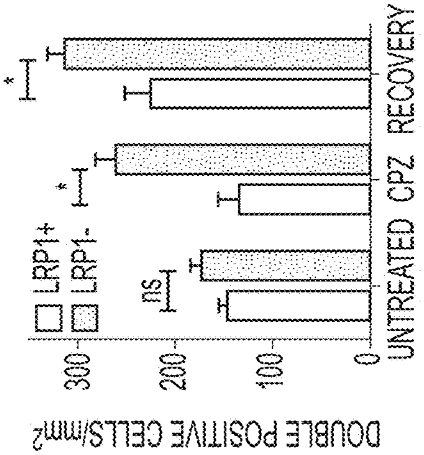

Example 6—OPC Numbers are Increased in Mice Lacking LRP1 During the Cuprizone Model The number of OPC in the corpus callosum are analyzed by staining the coronal sections with antibodies specific for PDGFR-α and Olig2 in either healthy mice, after 5 weeks of cuprizone diet, or 3 weeks post-removal of cuprizone from the diet. The number of OPC significantly increases in mice lacking LRP1 expression in OPC at 5 weeks after cuprizone start (Cpz bars, FIGS. 7A and B) and during remyelination (3 weeks post-cuprizone removal) (Recovery bars, FIG. 7B). Taken together, these data show that LRP1 deficiency induces expansion of OPC numbers during cuprizone-mediated demyelination.

Figure 8A:
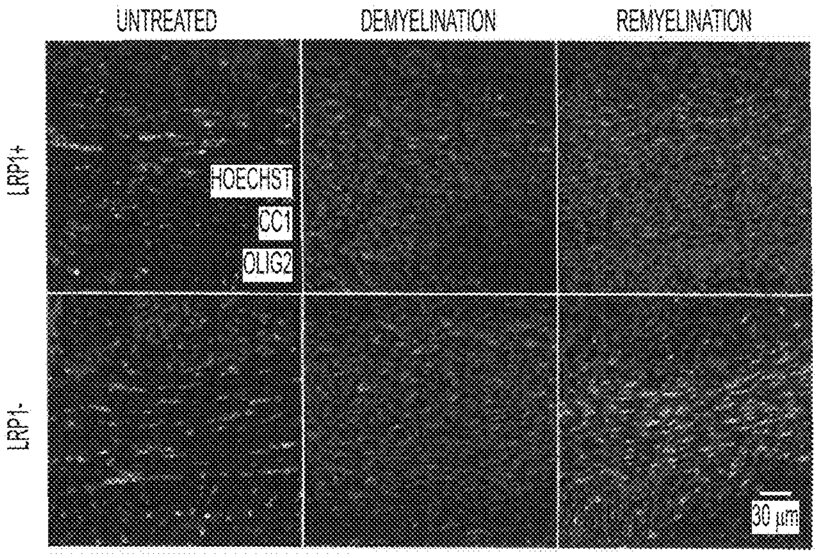
FIGS. 8A-8D show images of oligodendrocyte and OPC markers and graphs quantifying oligodendrocyte and OPC numbers in LRP1+ and LRP1− mice in a cuprizone model.
Figure 8B:
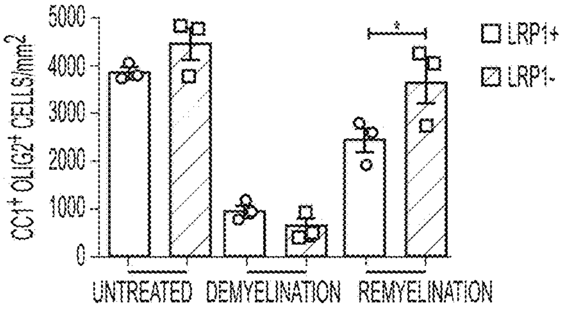
Figure 8C:
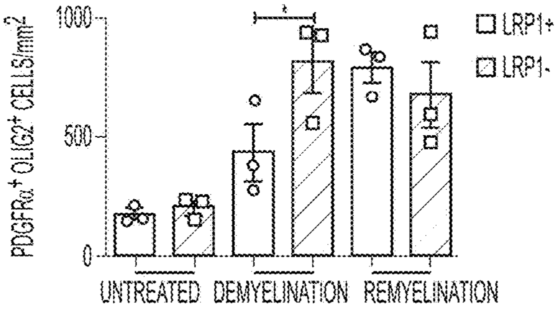
Figure 8D:
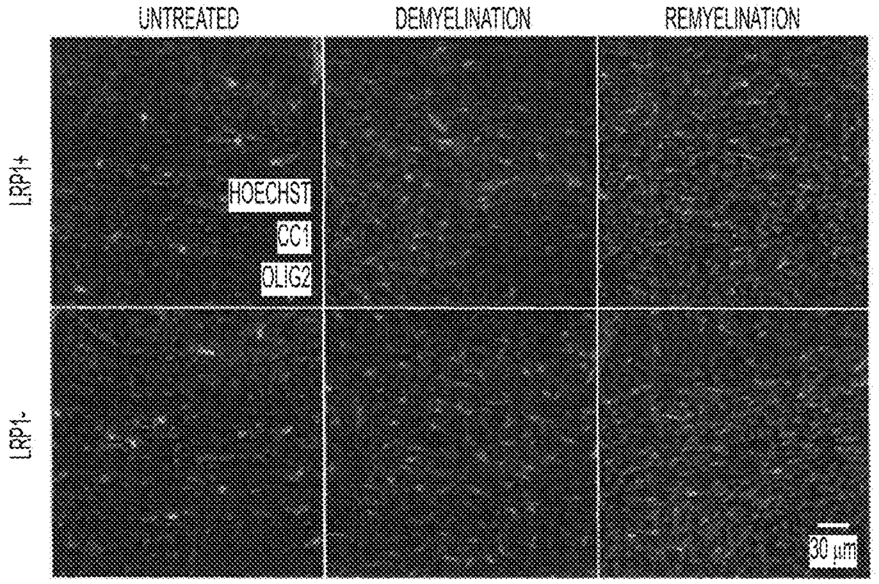

Example 7—Enhanced Remyelination and Greater OPC Number after Cuprizone Treatment in LRP1 Deficient Mice Remyelination is assessed again in LRP1+ and LRP1− mice using the cuprizone model. Mice are assessed before treatment (untreated), after 5 weeks of treatment with a 0.3% curpizone diet (demyelination), and 1 week after stopping cuprizone treatment (remyelination). FIG. 8A shows coronal sections of the corpus callosum stained for oligodendrocyte markers CC1 and Olig2. FIG. 8D shows coronal sections of the corpus callosum stained for the OPC markers PDGFR-α and Olig2. FIG. 8B is a graph showing the quantification of oligodendrocyte number in the corpus callosum of the mice (*P=0.0416, 2-way ANOVA, n=3 per genotype). FIG. 8C is a graph showing the quantification of OPC number in the corpus callosum of the mice (*P=0.0435, 2-way ANOVA, n=3 per genotype). LRP1+ mice are represented by the left bar in each pair; LRP1− mice are represented by the right bar in each pair in FIGS. 8B and 8C.

Example 8-Isolation and Characterization of Primary OPC

Figure 9A:
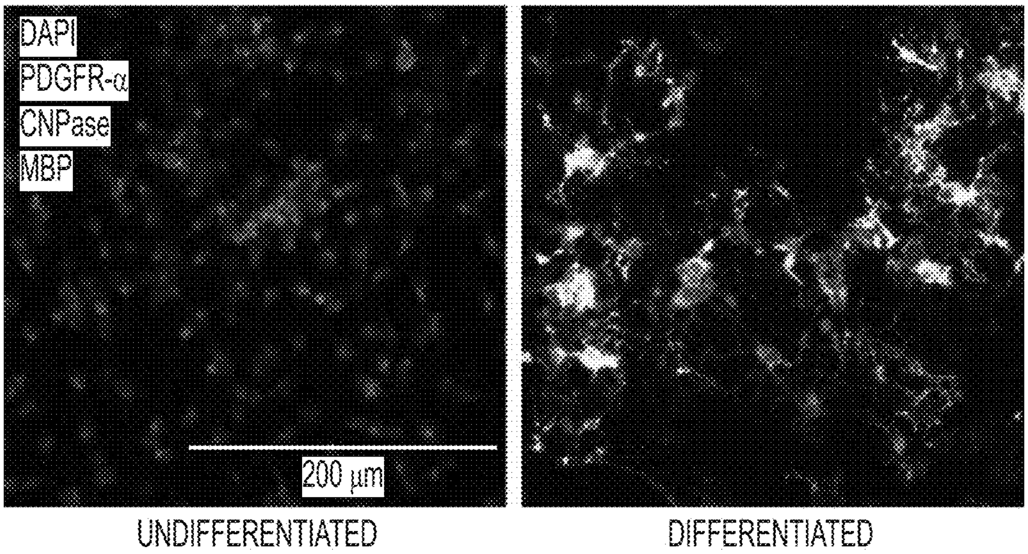
FIG. 9A shows an immunofluorescence analysis of PDGFR-α, CNPase and MBP expression.
Figure 9B:
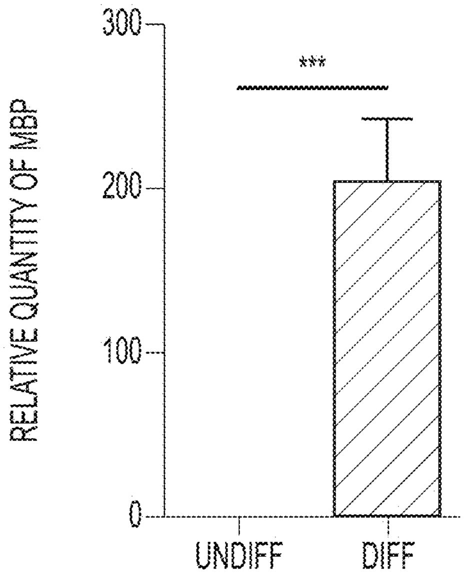
FIG. 9B shows a quantification of MBP expression based on qPCR analysis (P<0.001).

Primary cultures of mouse OPC are established by immunopanning as described in the art. OPC can be maintained at this immature stage, or be further induced to differentiate into oligodendrocytes by changing the culture conditions. As shown in FIG. 9A, left panel, undifferentiated cells isolated using the immuno-panning method are positive for PDGFR-α, as detected by immunofluorescence. After switching the culture into differentiation conditions, cells adopt the typical morphology of oligodendrocytes (FIG. 9A, right panel) and express CNPase and MBP, as demonstrated by immunofluorescence. OPC differentiation can also be monitored by qPCR analysis for MBP expression (FIG. 9B).

Example 9-LRP1 Silencing does not Affect OPC Viability In Vitro

To test if LRP1 contributes to cell viability, primary OPC are transfected with the SMARTpool siRNA against LRP1

Figure 10:
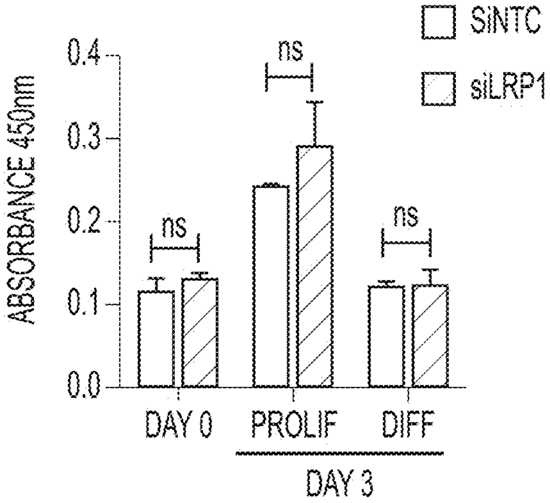
FIG. 10 shows CCK8 assay results, measuring dehydrogenase activity, in primary OPC transfected with siRNA-targeting LRP1 or a non-targeting control (siNTC).

(i.e., targeting sequences selected from SEQ ID NOs: 1-4) or a non-targeting control (NTC) siRNA and grown under conditions promoting proliferation or differentiation for 3 days. Overall viability is determined by a CCK8 assay, which measures dehydrogenase activity in living cells. The results are shown in FIG. 10. There is no significant difference in the OPC viability under either proliferative or differentiation conditions, which means LRP1 does not affect OPC viability in this system. Because the in vivo data indicate that OPC specific deletion of LRP1 results in an increase in OPC numbers during cuprizone-induced demyelination (shown in FIG. 7), this suggests that factor(s) present within the demyelination area, such as the myelin debris, affect OPC viability and/or proliferation in an LRP1 dependent manner.

Figure 11B:
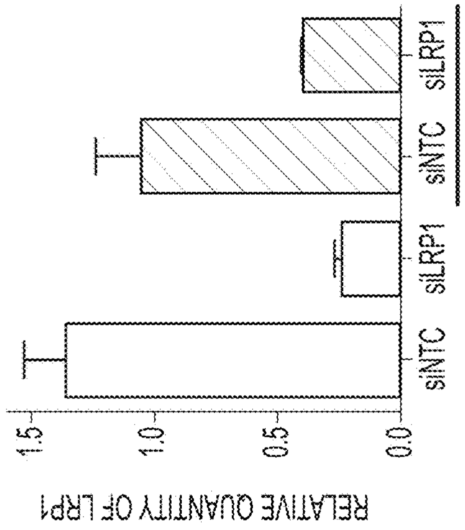
FIG. 11B shows qPCR expression of LRP1 in mouse OPC following silencing with siRNA.
Figure 11D:
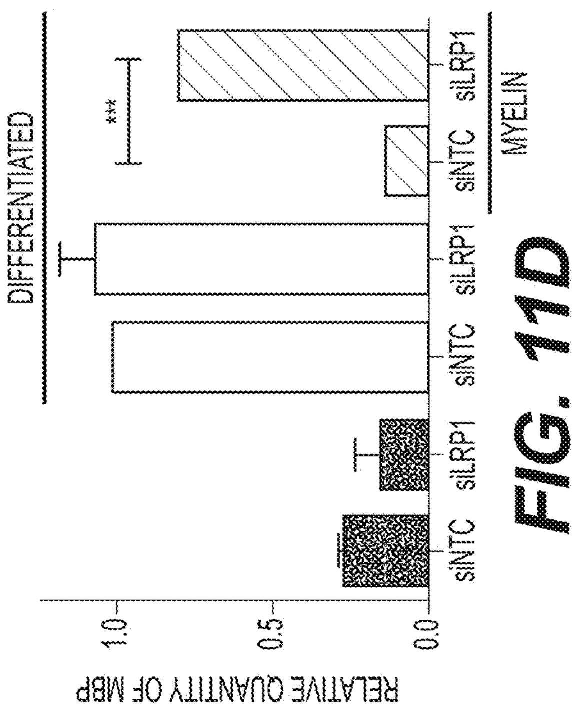
FIG. 11D shows qPCR analysis of MBP in differentiating rat OPC that have been silenced for LRP1 and grown in the presence or absence of myelin.
Figure 11A:
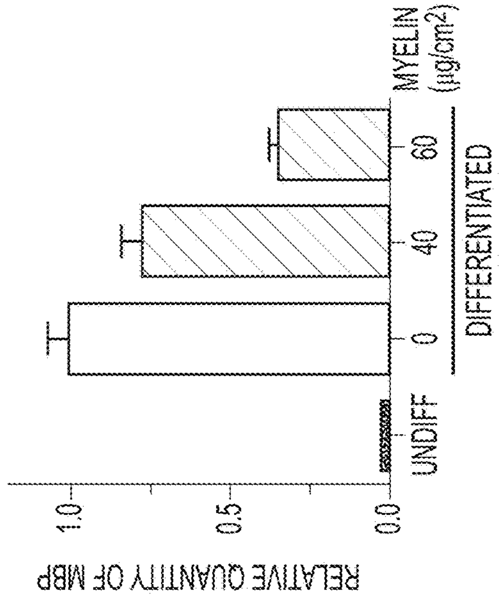
FIG. 11A shows the results of qPCR analysis for MBP of mouse OPC differentiated in the presence of increasing amount of myelin debris.
Figure 11C:
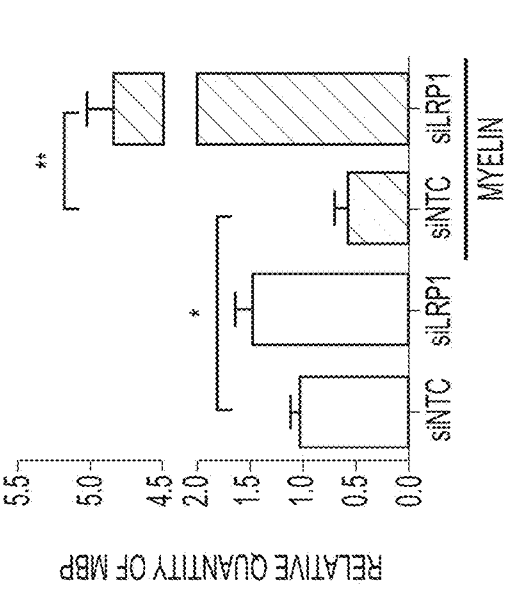
FIG. 11C shows qPCR analysis of MBP in differentiating mouse OPC that have been silenced for LRP1 and grown in the presence or absence of myelin.

Example 10-LRP1 Silencing Restores OPC Differentiation in the Presence of Myelin Purified myelin inhibits OPC differentiation into myelinating oligodendrocytes in a dose-dependent manner, as measured by qPCR analysis of MBP expression in primary OPC cultures, as described in the art and shown in FIG. 11A. Next, primary cultures of OPC are transfected with SMARTpool siRNA against LRP1 (siLRP1) (i.e., targeting sequences selected from SEQ ID NOs: 1-4) or a non-targeting control (siNTC), and switched to differentiation media in the presence or absence of purified myelin. After 72 hours, MBP expression is monitored by qPCR as a measure of OPC differentiation into oligodendrocytes (FIG. 11C). Again, adding myelin during differentiation inhibits expression of MBP by 40% (FIG. 11C, compare siNTC bars). However, if LRP1 expression in OPC is inhibited by siRNA, as verified by qPCR analysis (FIG. 11B, siLRP1), MBP expression increases even in the presence of myelin (FIG. 11C).

Next, these results are confirmed with murine OPC using rat OPC and the same experimental approach except using SMARTpool siLRP1 targeting sequences selected from SEQ ID NOs5-8. As with murine OPC, myelin debris also blocks expression of MBP during differentiation of rat OPC, as shown in FIG. 11D. Furthermore, downregulation of LRP1 with siRNA (60% silencing efficiency) is sufficient to bypass myelin inhibition and restore MBP expression. This is also shown in FIG. 11D. Taken together, inhibition of LRP1 in OPCs allows the cells to overcome myelin inhibition and differentiate into mature oligodendrocytes in vitro.

Figure 12:
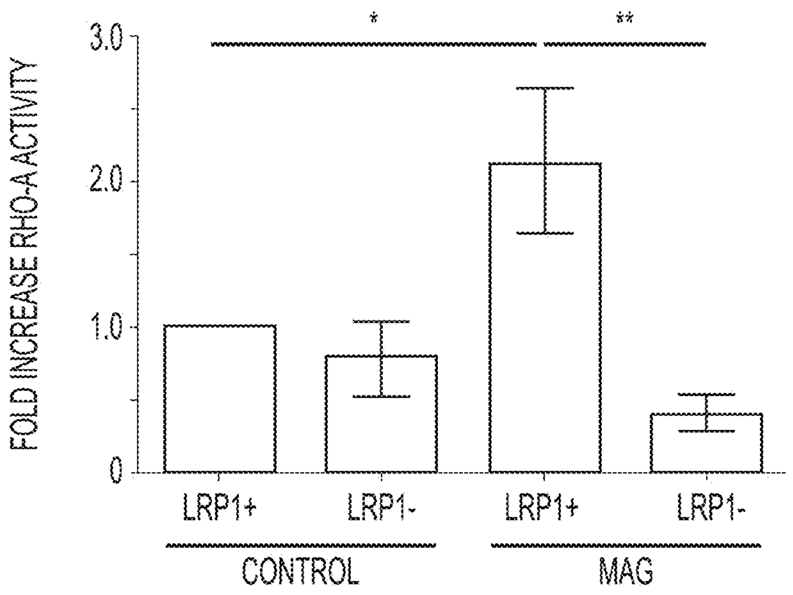
FIG. 12 shows the level of Rho-A activity in LRP1+ and LRP1-neuronal cells treated with purified MAG.

Example 11—LRP1-p75NTR Receptor Complex Mediates Myelin Inhibitory Signaling in Neurons Following nerve injury, myelin debris can block axonal regeneration by binding to the p75NTR receptor and activating the small GTPase Rho-A. LRP1 recognizes myelin inhibitory proteins and forms a signaling complex with p75NTR to initiate Rho-A activation in neurons and inhibit axonal regeneration. As shown in FIG. 12, MAG, a myelin protein that mediates inhibition of axonal regeneration following injury, induces a robust activation of Rho-A in a neuronal cell line. However, increased Rho-A activity is not detected if LRP1 is silenced, demonstrating that LRP1 is necessary to initiate Rho-A activation downstream of MAG.

Example 12—OPC Phagocytose Myelin Debris

Figure 13:
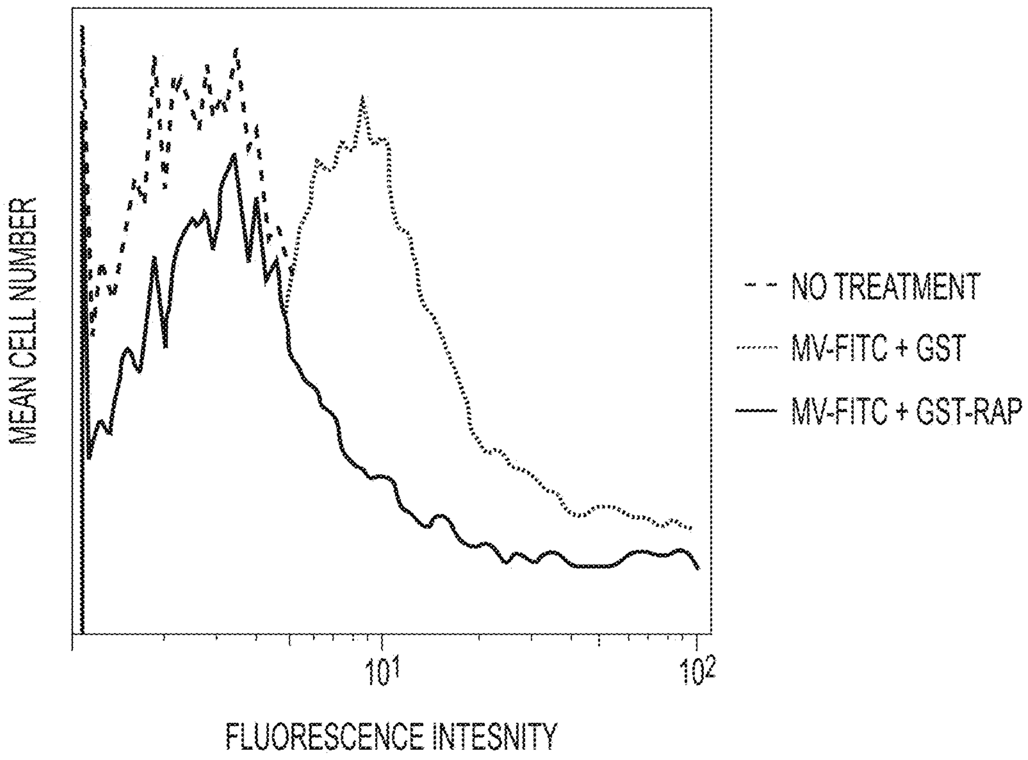
FIG. 13 shows flow cytometry analysis of internalization of myelin by OPC.

Primary cultures of OPC are incubated with purified myelin labeled with FITC for 30 min, after which the cells are extensively washed and treated with pronase to proteolitically release extracellularly associated fluorescent myelin. Cells are next analyzed by flow cytometry to monitor internalization. As shown in FIG. 13, OPC can phagocytose labeled myelin in vitro. Furthermore, blocking LRP1 with RAP, an LRP1 antagonist, completely blocks internalization of myelin vesicles.

Example 13—Experimental Autoimmune Encephalomyelitis

Figure 14:
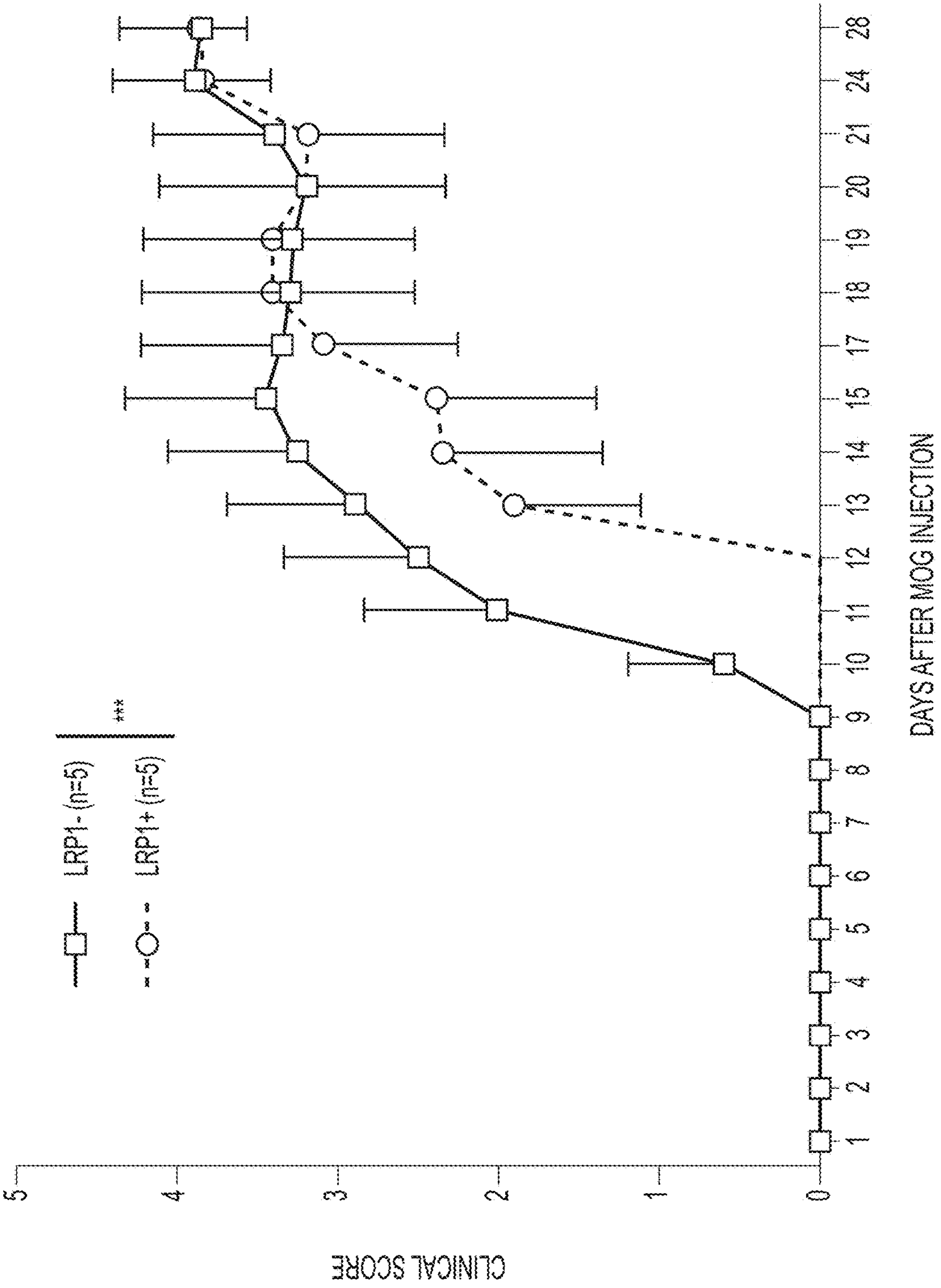
FIG. 14 shows EAE model progression in LRP1+ and LRP1− mice.

Experimental Autoimmune Encephalomyelitis (EAE) is a mouse model of MS. LRP1+ OPC and LRP1− OPC mice are injected with myelin oligodendrocyte glycoprotein (MOG) to induce demyelination. Mice are then scored on the following clinical scale: 0-no abnormality, 1-limp tail, 2-mild hindlimb weakness, 3-severe hindlimb weakness, 4-complete hindlimb paralysis, 5-moribund or dead. The results are shown in FIG. 14. Mice lacking LRP1 expression in OPC (LRP1−) have a delayed onset of disease when compared to control mice (LRP1+). Based on these results, mice lacking LRP1 in OPC can have increased myelination, when compared to controls, and can have less disease during EAE.

While these methods, compositions, and other features have been disclosed with reference to specific embodiments, it is apparent that other embodiments and variations of this disclosure may be devised by others skilled in the art without departing from the true spirit and scope of the disclosure.

What is claimed is:

1. A genetically modified mouse whose genome comprises:

(i) in cells other than oligodendrocytes and oligodendrocyte precursors, an endogenous low density lipoprotein-related protein 1 (LRP1) gene flanked by lox P sites;

(ii) a nucleic acid sequence encoding Cre recombinase operably linked to an Oligo 1 promoter; and (iii) in oligodendrocytes and oligodendrocyte precursors, a deletion of the endogenous LRP1 gene via action of the Cre recombinase on the lox P sites, wherein the mouse is capable of exhibiting increased myelination upon being fed a cuprizone diet as compared to a control mouse that expresses LRP1 in its oligodendrocytes and oligodendrocyte precursors subjected to a cuprizone diet, or is capable of exhibiting delayed onset of experimental autoimmune encephalomyelitis (EAE) upon being exposed to EAE induction as compared to a control mouse that expresses LRP1 in its oligodendrocytes and oligodendrocyte precursors exposed to EAE induction.

2. An isolated oligodendrocyte precursor whose genome comprises an inactivated LRP1 gene, wherein the isolated oligodendrocyte precursor is obtained from the mouse of claim 1.

3. A method of isolating an oligodendrocyte precursor, the method comprising:

isolating an oligodendrocyte precursor whose genome comprises an inactivated LRP1 gene from the mouse of claim 1.

* * * * *